(12) United States Patent
Bender et al.

(10) Patent No.: US 7,541,351 B2
(45) Date of Patent: Jun. 2, 2009

(54) COMPOUNDS FOR THE TREATMENT OF HEPATITIS C

(75) Inventors: John A. Bender, Middletown, CT (US); Min Ding, Glastonbury, CT (US); Robert G. Gentles, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/971,362

(22) Filed: Jan. 9, 2008

(65) Prior Publication Data

US 2008/0171015 A1 Jul. 17, 2008

Related U.S. Application Data

(60) Provisional application No. 60/884,459, filed on Jan. 11, 2007.

(51) Int. Cl.
  *A61P 31/00* (2006.01)
  *A61K 31/55* (2006.01)
  *C07D 223/14* (2006.01)
(52) U.S. Cl. .................. 514/214.01; 540/576
(58) Field of Classification Search ............ 514/214.01; 540/576
  See application file for complete search history.

(56) References Cited

U.S. PATENT DOCUMENTS

| 7,153,848 | B2 | 12/2006 | Hudyma et al. | 514/214.01 |
| 7,348,425 | B2 | 3/2008 | Hudyma et al. | 540/576 |
| 2007/0060565 | A1 | 3/2007 | Meanwell et al. | 514/214.01 |
| 2007/0078122 | A1 | 4/2007 | Bergstrom et al. | 514/214.01 |
| 2007/0184024 | A1 | 8/2007 | Meanwell et al. | 424/85.2 |
| 2007/0185083 | A1 | 8/2007 | Bergstrom et al. | 514/214.01 |
| 2007/0270405 | A1 | 11/2007 | Bender et al. | 514/214.01 |
| 2007/0270406 | A1 | 11/2007 | Gentles et al. | 514/214.01 |
| 2007/0275930 | A1 | 11/2007 | Gentles et al. | 514/79 |
| 2007/0275947 | A1 | 11/2007 | Bergstrom | 514/211.15 |
| 2007/0287694 | A1 | 12/2007 | Yeung et al. | 514/210.21 |

FOREIGN PATENT DOCUMENTS

| WO | WO 2005/080399 | 9/2005 |
| WO | WO 2006/046030 | 5/2006 |
| WO | WO 2006/046039 | 5/2006 |
| WO | WO 2007/029029 | 3/2007 |
| WO | WO 2007/129119 | 11/2007 |

OTHER PUBLICATIONS

U.S. Appl. No. 12/022,541, filed Jan. 30, 2008, Kap-Sun Yeung et al.
U.S. Appl. No. 12/046,030, filed Mar. 11, 2008, Kap-Sun Yeung et al.
U.S. Appl. No. 12/039,239, filed Feb. 28, 2008, Robert G. Gentles et al.
U.S. Appl. No. 12/045,874, filed Mar. 11, 2008, Robert G. Gentles et al.
U.S. Appl. No. 12/045,766, filed Mar. 11, 2008, John A. Bender et al.
U.S. Appl. No. 12/041,072, filed Mar. 3, 2008, Kap-Sun Yeung et al.
U.S. Appl. No. 12/031,844, filed Feb. 15, 2008, Andrew Nickel et al.
U.S. Appl. No. 11/942,285, filed Nov. 19, 2007, John A. Bender et al.
U.S. Appl. No. 12/046,286, filed Mar. 11, 2008, Piyasena Hewawasam, et al.

*Primary Examiner*—Brenda L Coleman
(74) *Attorney, Agent, or Firm*—James Epperson

(57) ABSTRACT

The invention encompasses compounds of formula I as well as compositions and methods of using the compounds. The compounds have activity against hepatitis C virus (HCV) and are useful in treating those infected with HCV.

11 Claims, No Drawings

COMPOUNDS FOR THE TREATMENT OF HEPATITIS C

CROSS REFERENCE TO RELATED APPLICATIONS

This application claims the benefit of U.S. Provisional Application Ser. No. 60/884,459, filed Jan. 11, 2007.

BACKGROUND OF THE INVENTION

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

DESCRIPTION OF THE INVENTION

One aspect of the invention is a compound of formula I

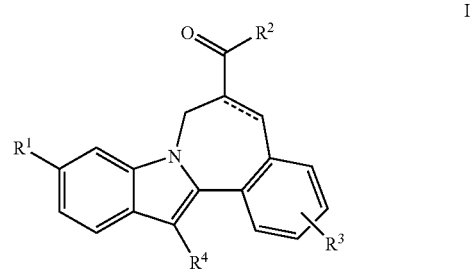

where:
$R^1$ is $CO_2R^5$ or $CONR^6R^7$;
$R^2$ is

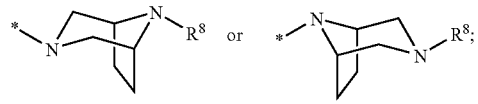

$R^3$ is hydrogen, halo, alkyl, alkenyl, hydroxy, benzyloxy, alkoxy, or haloalkoxy;
$R^4$ is cycloalkyl;
$R^5$ is hydrogen or alkyl;
$R^6$ is hydrogen, alkyl, alkylSO$_2$, cycloalkylSO$_2$, haloalkylSO$_2$, $(R^9)_2NSO_2$, or $(R^{10})SO_2$;
$R^7$ is hydrogen or alkyl;
$R^8$ is hydrogen, alkyl, cycloalkyl, (cycloalkyl)alkyl, alkylcarbonyl, alkoxycarbonyl, benzyl, benzyloxycarbonyl, or pyridinyl;
$R^9$ is hydrogen or alkyl;
$R^{10}$ is azetidinyl, pyrrolidinyl, piperidinyl, N—($R^{11}$)piperazinyl, morpholinyl, thiomorpholinyl, homopiperidinyl, or homomorpholinyl;
$R^{11}$ is hydrogen or alkyl; and
the dotted line represents a single bond or a double bond;

or a pharmaceutically acceptable salt thereof.

Another aspect of the invention is a compound of formula I where $R^1$ is $CONR^6R^7$; $R^6$ is alkylSO$_2$, cycloalkylSO$_2$, haloalkylSO$_2$, $(R^9)_2NSO_2$, or $(R^{10})SO_2$; and $R^7$ is hydrogen.

Another aspect of the invention is a compound of formula I where $R^3$ is hydrogen.

Another aspect of the invention is a compound of formula I where $R^3$ is methoxy.

Another aspect of the invention is a compound of formula I where $R^4$ is cyclohexyl.

Another aspect of the invention is a compound of formula I where $R^6$ is $(R^9)_2NSO_2$ or $(R^{10})SO_2$.

Another aspect of the invention is a compound of formula I where the dotted line represents a single bond as in the following structural formula.

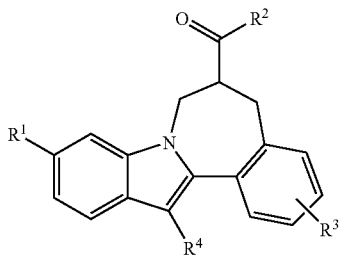

Another aspect of the invention is a compound of formula I with the following stereochemistry.

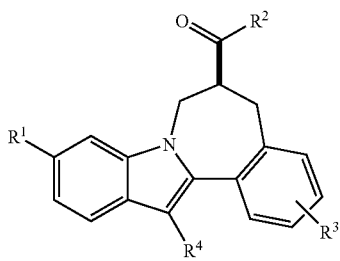

Another aspect of the invention is a compound of formula I with the following stereochemistry.

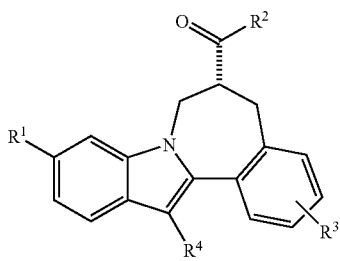

Another aspect of the invention is a compound of formula I where the dotted line represents a double bond as in the following structural formula.

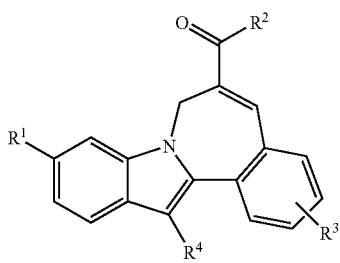

Any scope of any variable, including $R^1$, $R^2$, $R^3$, $R^4$, $R^5$, $R^6$, $R^7$, $R^8$, $R^9$, $R^{10}$, $R^{11}$ and the dotted line can be used independently with the scope of any other variable.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy," and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (for example, the structures below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods known in the art.

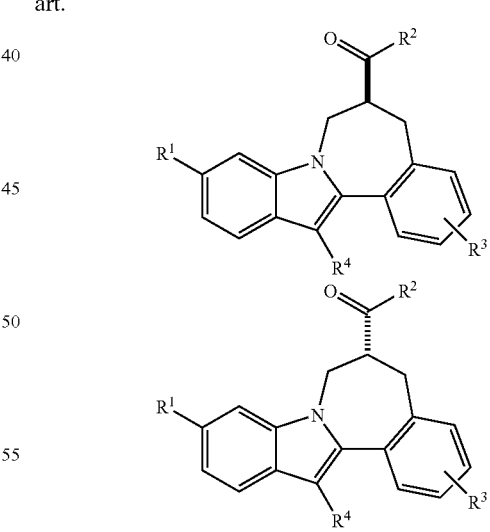

Synthetic Methods

The compounds may be made by methods known in the art including those described below. Some reagents and intermediates are known in the art. Other reagents and intermediates can be made by methods known in the art using commercially available materials. The variables (e.g. numbered "R" substituents) used to describe the synthesis of the compounds are intended only to illustrate how to make and are not to be confused with variables used in the claims or in other sections of the specification. Abbreviations used within the schemes generally follow conventions used in the art.

Methyl 2-bromo-3-cyclohexyl-1H-indole-6-carboxylate can be hydrolyzed to 2-bromo-3-cyclohexyl-1H-indole-6-carboxylic acid (See Scheme 1). This compound can be condensed with a variety of sulfonyl ureas, using for example, 1,1'-carbonyldiimidazole in combination with 1,8-diazabicyclo[5.4.0]undec-7-ene in anhydrous THF. The resultant acyl sulfamides can be subjected to known coupling reactions with a diversity of 2-formyl boronic acids or esters, using for example, Suzuki coupling conditions, to provide cyclic hemiaminal intermediates of the type depicted. These compounds can be converted to indolobenzazepines derivatives by treatment with methyl 2-(dimethoxyphosphoryl)acrylate under the influence of cesium carbonate in DMF via consecutive Michael and Horner Emmons reactions.

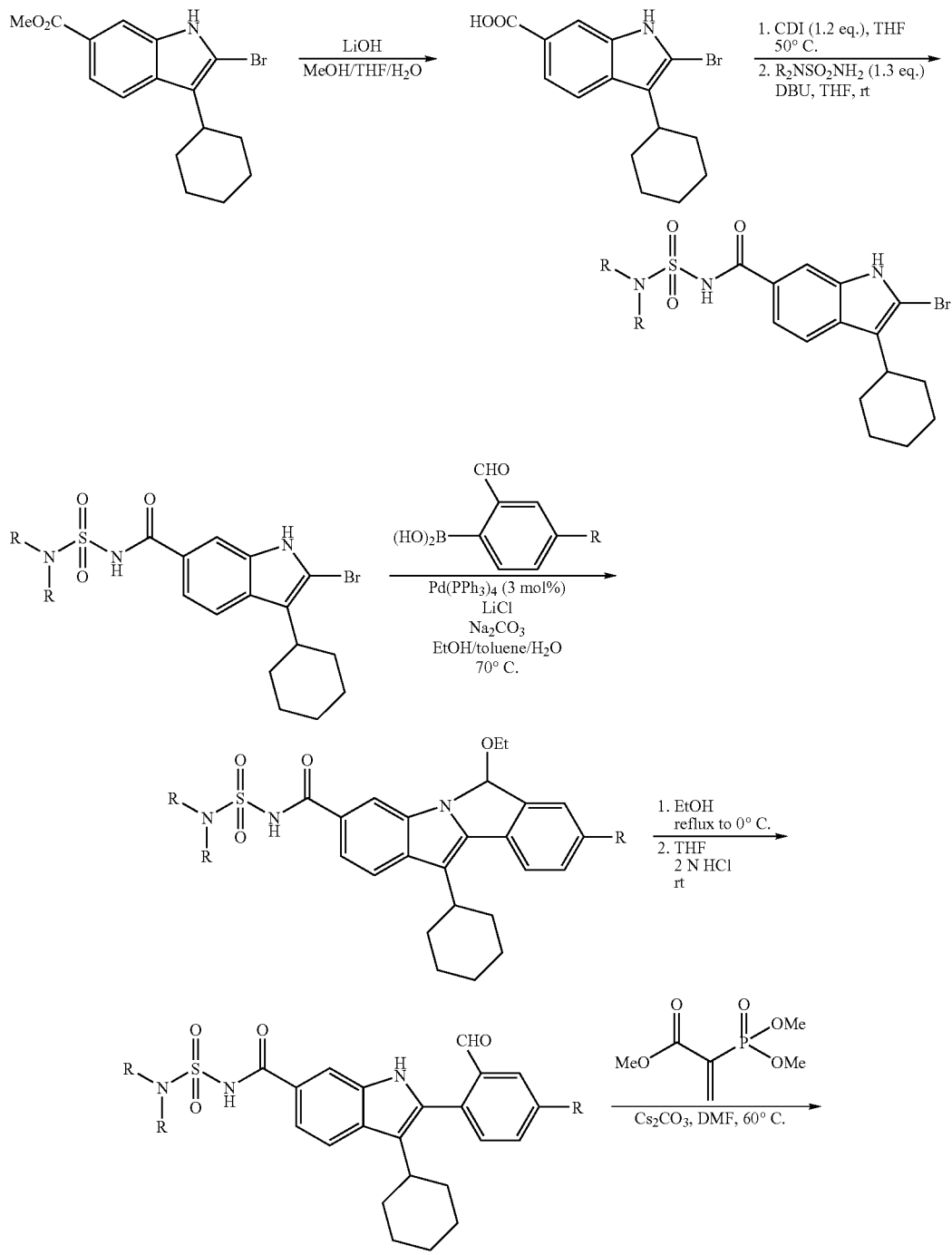

Scheme 1.

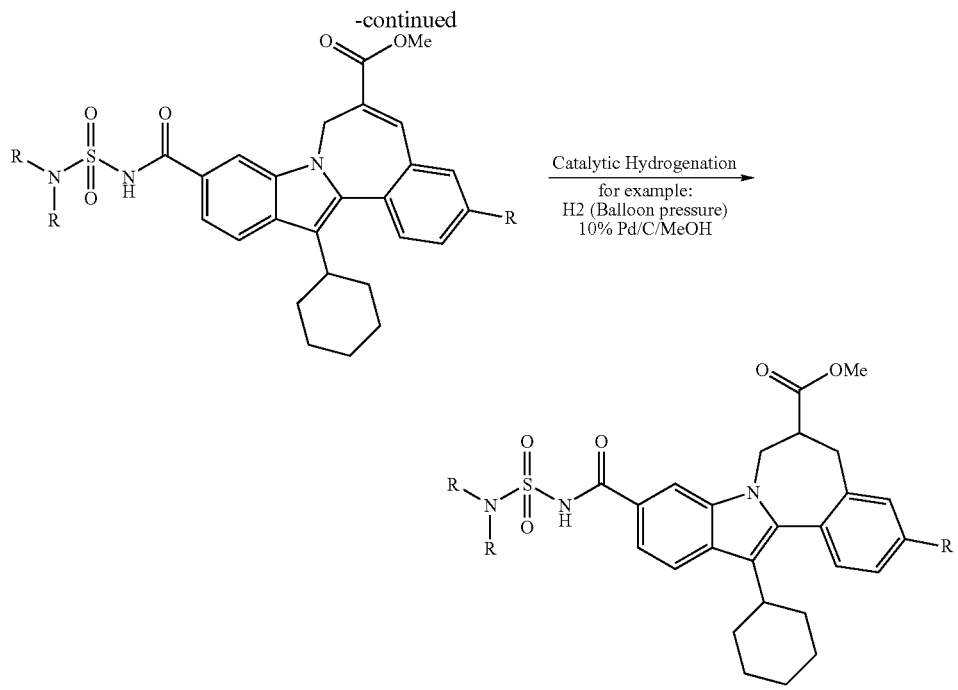
N-protected piperazines can also be coupled to the intermediate indolobenzazepine acids and the resultant piperazine carboxamides can be deprotected using methods known in the art and derivatized using a variety of synthetic protocols, some illustrative examples of which are shown below (See Scheme 2).
Scheme 2.
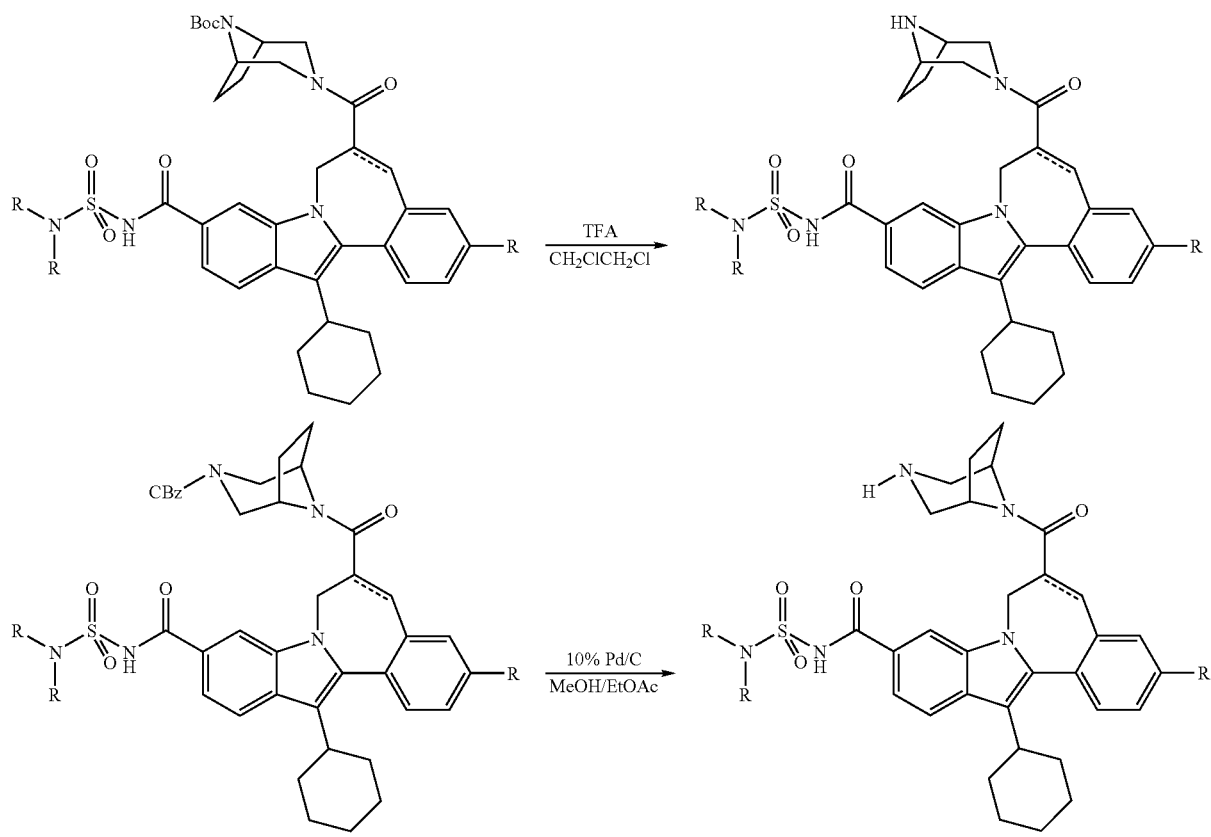

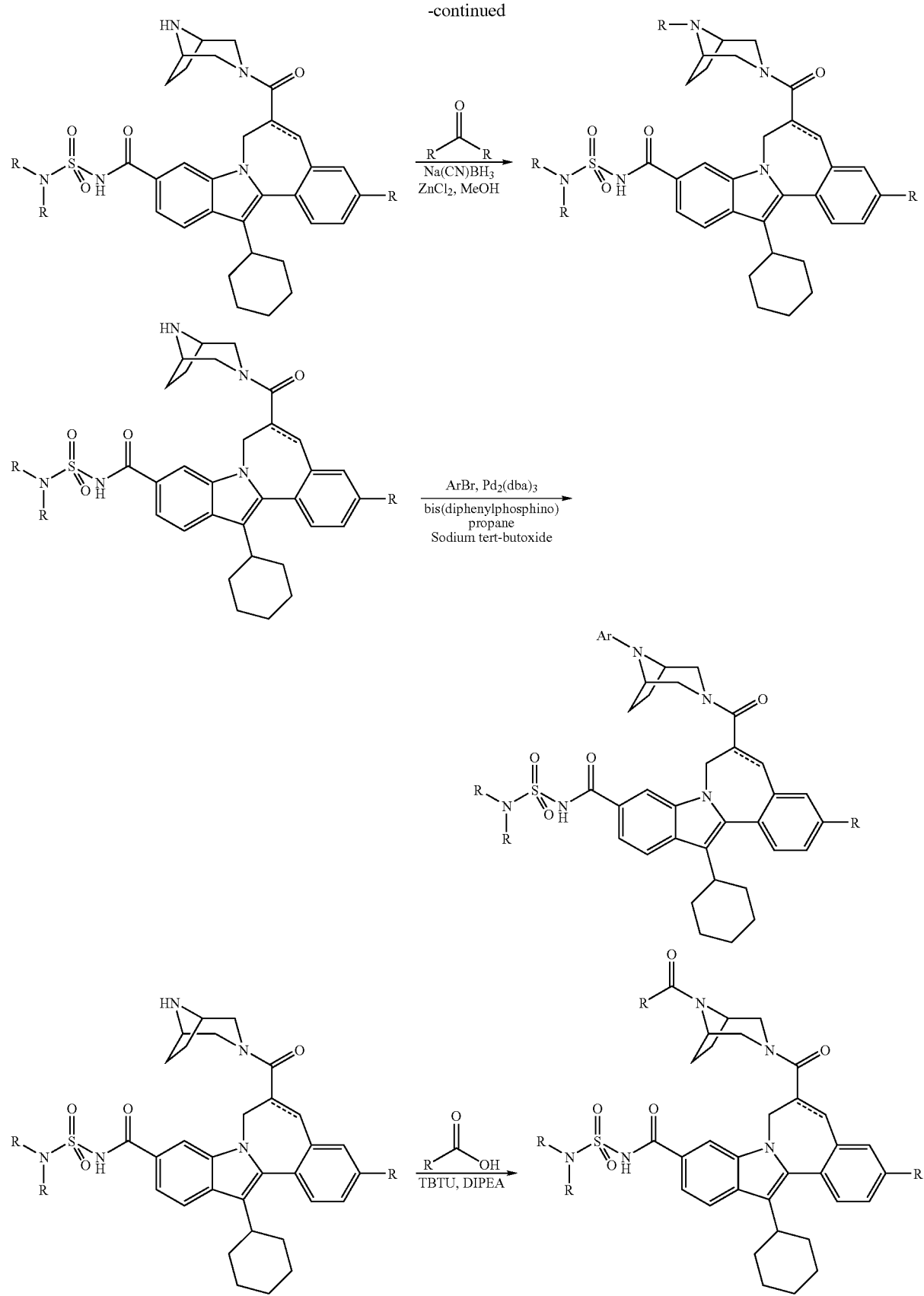

An intermediate useful for the synthesis of some compounds of the invention involves the preparation of the tert-butyl ester indolobenzazepine shown in Scheme 3.

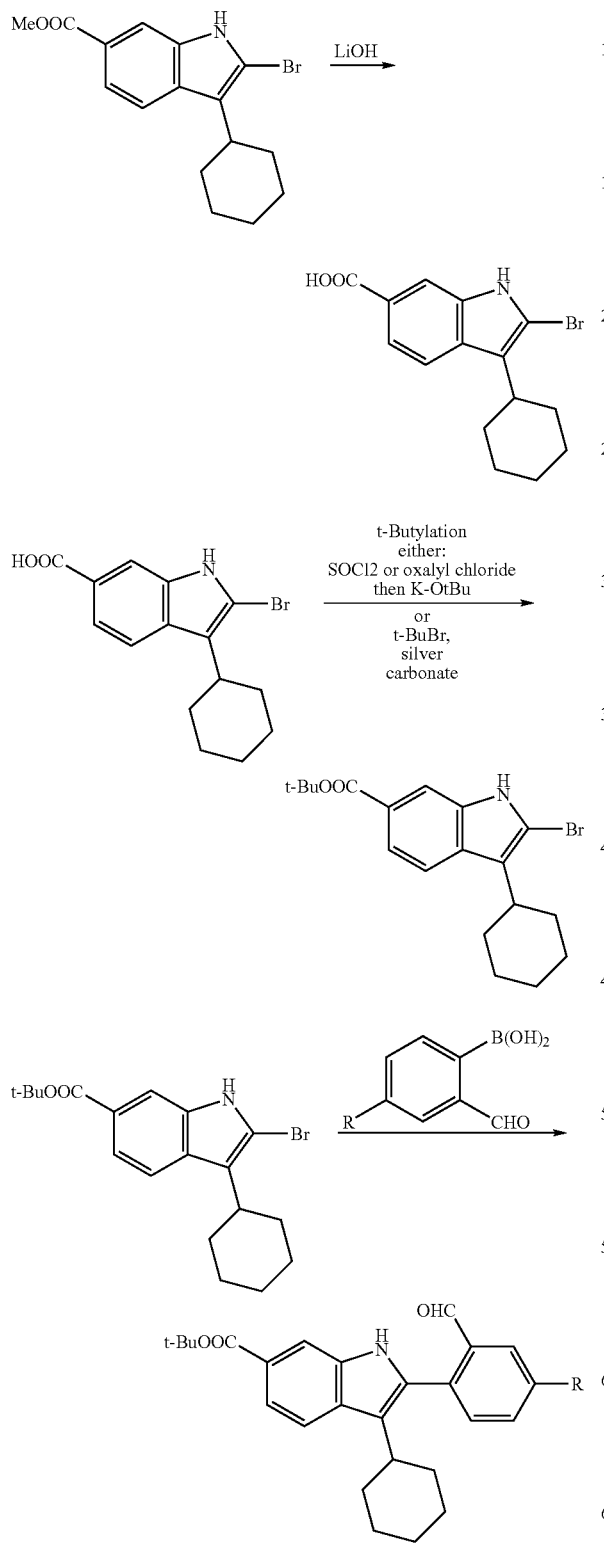

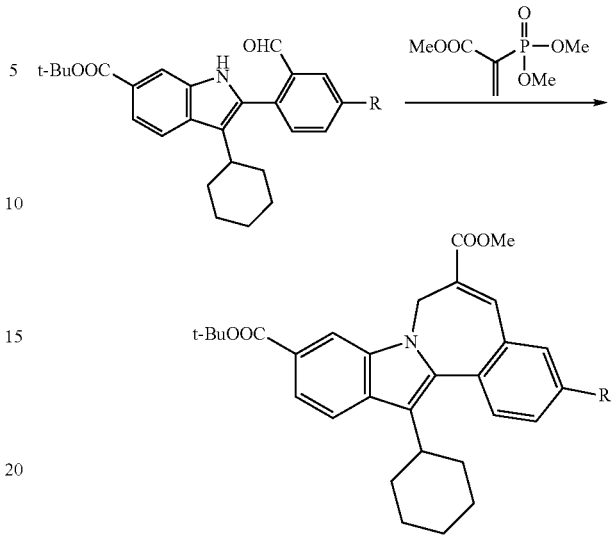

This methodology involves base catalyzed hydrolysis of the indole methyl ester shown, followed by t-butoxide ester formation (for example, reaction with either thionyl chloride and potassium tertiary butoxide or alkylation with silver carbonate and tertiary butyl bromide). The resultant compound can be transformed using chemistry analogous to that outlined previously to provide the mixed ester indolobenzazepines shown above.

These intermediates are useful in an alternative procedure that can be employed for the preparation of acylsulfamide and acylsulfonamide alkyl-bridged piperazines as shown in Scheme 4. Cleavage of the t-butyl ester group can generate the acid which can be coupled to a diversity of sulfonamides and sulfonylureas. Subsequent hydrolysis affords the related aliphatic acid, which can be coupled with a diversity of alkyl-bridged piperazines. For example, O-(1H-benzotriazol-1-yl)-N,N,N',N'-tetramethyluronium tetrafluoroborate and diisopropyl ethyl amine in DMSO can give the alkyl bridged piperazine carboxamides.

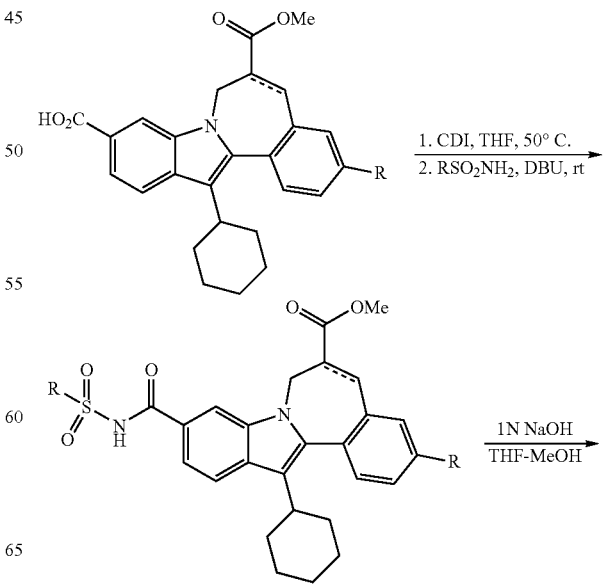

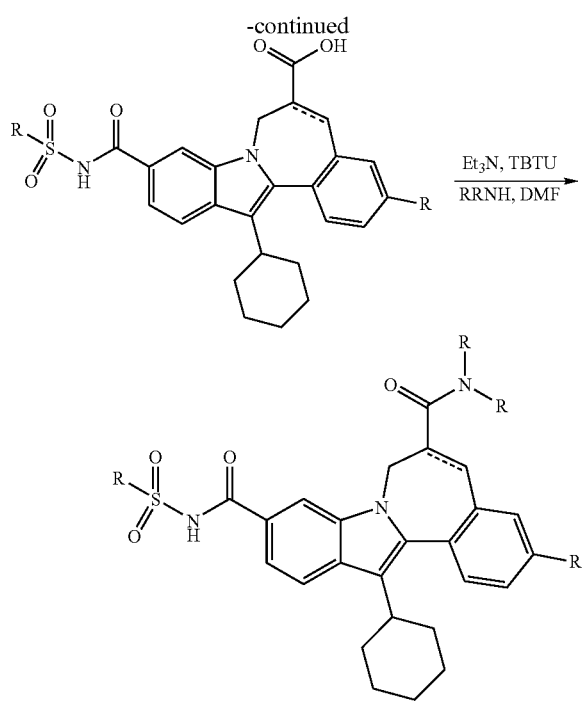

Biological Methods

The compounds demonstrated activity against HCV NS5B as determined in the following HCV RdRp assays.

HCV NS5B RdRp cloning, expression, and purification. The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21 (DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 μg/ml and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM MgCl2, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 μm filter unit (Corning).

The protein was purified using three sequential chromatography steps: Heparin sepharose CL-6B, polyU sepharose 4B, and Hitrap SP sepharose (Pharmacia). The chromatography buffers were identical to the lysis buffer but contained no lysozyme, deoxyribonuclease I, MgCl2 or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

Standard HCV NS5B RdRp enzyme assay. HCV RdRp genotype 1b assays were run in a final volume of 60 μl in 96 well plates (Costar 3912). The assay buffer is composed of 20 mM Hepes, pH 7.5, 2.5 mM KCl, 2.5 mM MgCl2, 1 mM DTT, 1.6 U RNAse inhibitor (Promega N2515), 0.1 mg/ml BSA (Promega R3961), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT 12 primer was used at 180 nM final concentration. Template was obtained commercially (Amersham 27-4110). Biotinylated primer was prepared by Sigma Genosys. 3H-UTP was used at 0.6 μCi (0.29 μM total UTP). Reactions were initiated by the addition of enzyme, incubated at 30° C. for 60 min, and stopped by adding 25 μl of 50 mM EDTA containing SPA beads (4 μg/μl, Amersham RPNQ 0007). Plates were read on a Packard Top Count NXT after >1 hr incubation at room temperature.

Modified HCV NS5B RdRp enzyme assay. A modified enzyme assay was performed essentially as described for the standard enzyme assay except for the following: The biotinylated oligo dT12 primer was precaptured on streptavidin-coated SPA beads by mixing primer and beads in assay buffer and incubating at room temperature for one hour. Unbound primer was removed after centrifugation. The primer-bound beads were resuspended in 20 mM Hepes buffer, pH 7.5 and used in the assay at final concentrations of 20 nM primer and 0.67 μg/μl beads. Order of addition in the assay: enzyme (14 nM) was added to diluted compound followed by the addition of a mixture of template (0.2 nM), 3H-UTP (0.6 μCi, 0.29 μM), and primer-bound beads, to initiate the reaction; concentrations given are final. Reactions were allowed to proceed for 4 hours at 30° C.

$IC_{50}$ values for compounds were determined using seven different [I]. $IC_{50}$ values were calculated from the inhibition using the formula $y=A+((B-A)/(1+((C/x)^D)))$.

FRET Assay Preparation. To perform the HCV FRET screening assay, 96-well cell culture plates were used. The FRET peptide (Anaspec, Inc.) (Taliani et al., *Anal. Biochem.* 1996, 240, 60-67) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The assay reagent was made as follows: 5× cell Luciferase cell culture lysis reagent from Promega (#E153A) diluted to 1× with dH2O, NaCl added to 150 mM final, the FRET peptide diluted to 20 μM final from a 2 mM stock.

To prepare plates, HCV replicon cells, with or without a *Renilla* luciferase reporter gene, were trypsinized and placed into each well of a 96-well plate with titrated test compounds added in columns 3 through 12; columns 1 and 2 contained a control compound (HCV protease inhibitor), and the bottom row contained cells without compound. The plates were then placed in a CO2 incubator at 37° C.

Assays. Subsequent to addition of the test compounds described above (FRET Assay Preparation), at various times the plate was removed and Alamar blue solution (Trek Diagnostics, #00-100) was added per well as a measure of cellular toxicity. After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for 20 cycles and the plate read in a kinetic mode. Typically, the signal to noise using an endpoint analysis after the reads was at least three-fold. Alternatively, after Alamar blue reading, plates were rinsed with PBS, 50 ul of DMEM (high glucose) without phenol red was added and plates were then used for luciferase assay using the Promega Dual-Glo Luciferase Assay System.

Compound analysis was determined by quantification of the relative HCV replicon inhibition and the relative cytotoxicity values. To calculate cytoxicity values, the average Alamar Blue fluorescence signals from the control wells were set as 100% non-toxic. The individual signals in each of the compound test wells were then divided by the average control signal and multiplied by 100% to determine percent cytotoxicity. To calculate the HCV replicon inhibition values, an average background value was obtained from the two wells containing the highest amount of HCV protease inhibitor at the end of the assay period. These numbers were similar to those obtained from naïve Huh-7 cells.

The background numbers were then subtracted from the average signal obtained from the control wells and this number was used as 100% activity. The individual signals in each of the compound test wells were then divided by the averaged control values after background subtraction and multiplied by 100% to determine percent activity. $EC_{50}$ values for a protease inhibitor titration were calculated as the concentration which caused a 50% reduction in FRET or luciferase activity. The two numbers generated for the compound plate, percent cytoxicity and percent activity were used to determine compounds of interest for further analysis.

Representative data for compounds are reported in Table 1.

TABLE 1

| Structure | $IC_{50}$ | $EC_{50}$ |
|---|---|---|
| | B | B |
| | B | B |
| | B | B |

TABLE 1-continued
| Structure | IC$_{50}$ | EC$_{50}$ |
|---|---|---|
| 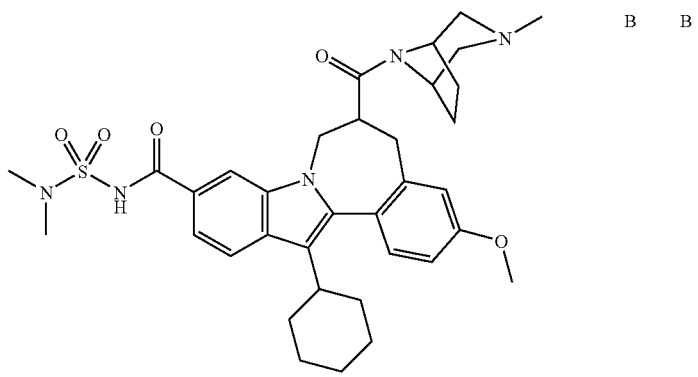 | B | B |
| 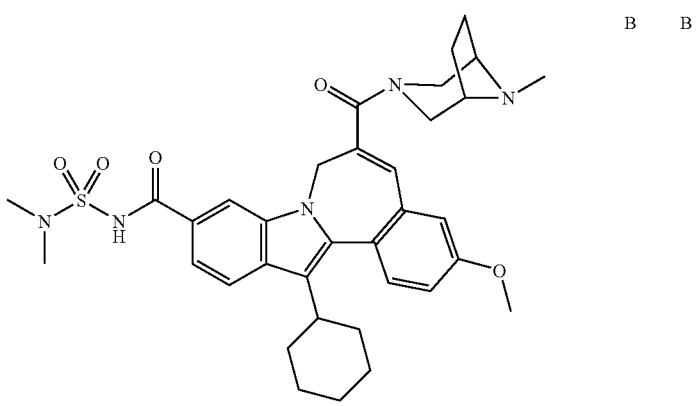 | B | B |
| 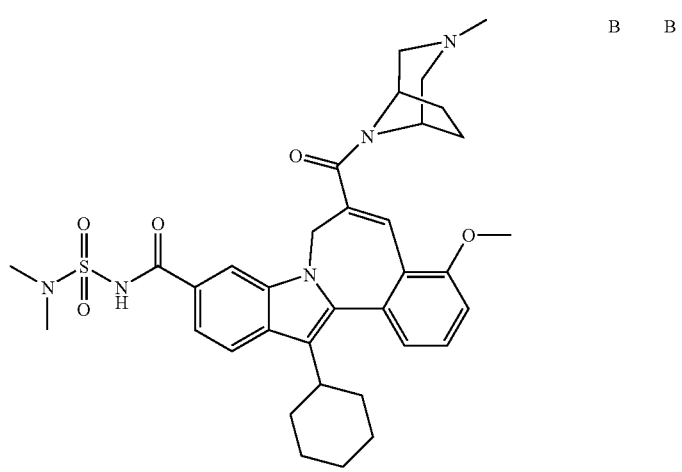 | B | B |

TABLE 1-continued
| Structure | IC$_{50}$ | EC$_{50}$ |
|---|---|---|
| 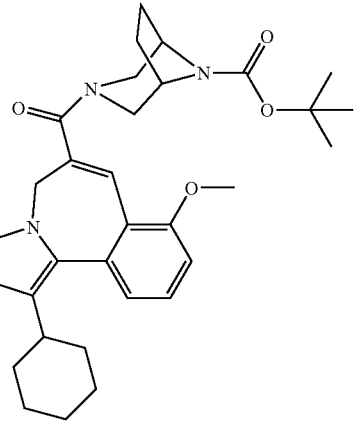 | B | B |
| 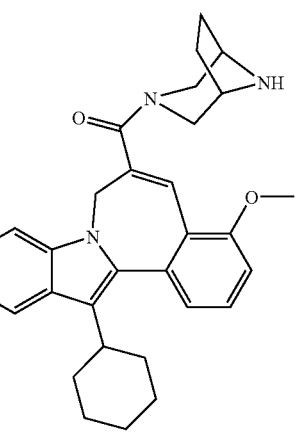 | B | B |
| 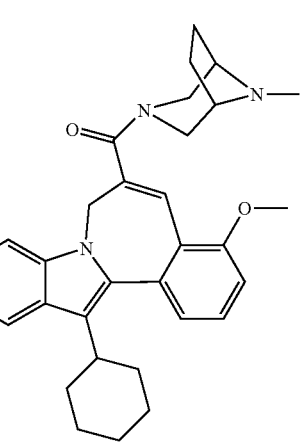 | B | B |

TABLE 1-continued
| Structure | IC$_{50}$ | EC$_{50}$ |
|---|---|---|
| 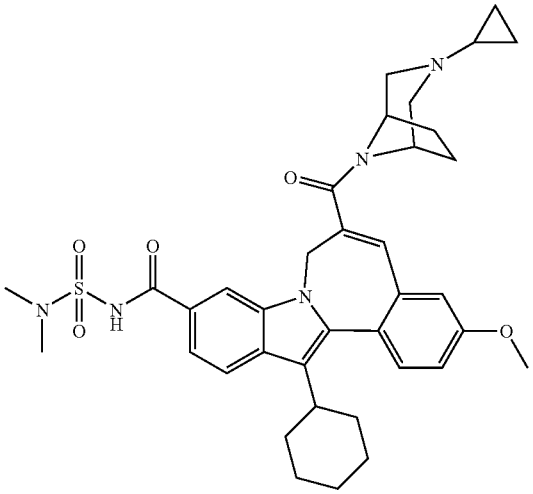 | C | B |
| 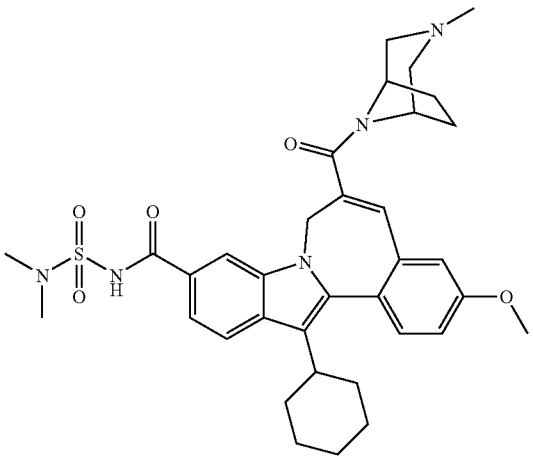 | B | B |
| 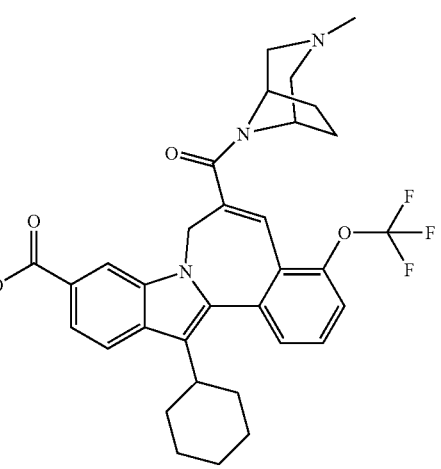 | A | A |

TABLE 1-continued
| Structure | IC$_{50}$ | EC$_{50}$ |
|---|---|---|
| 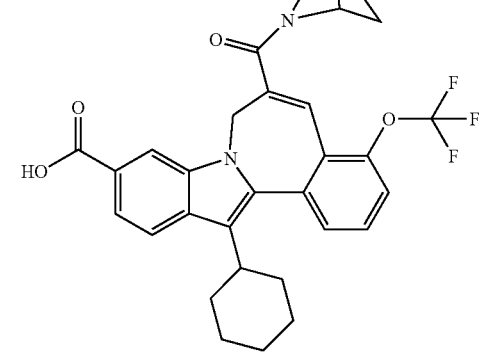 | ND | ND |
| 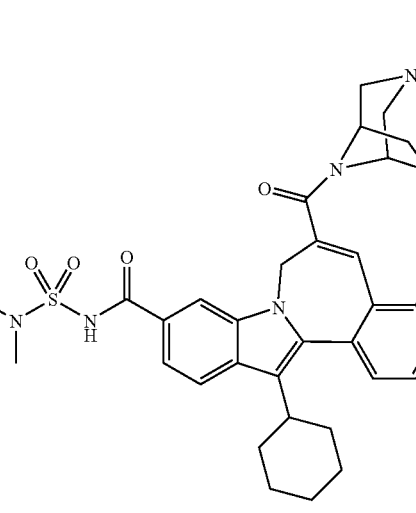 | A | A |
| 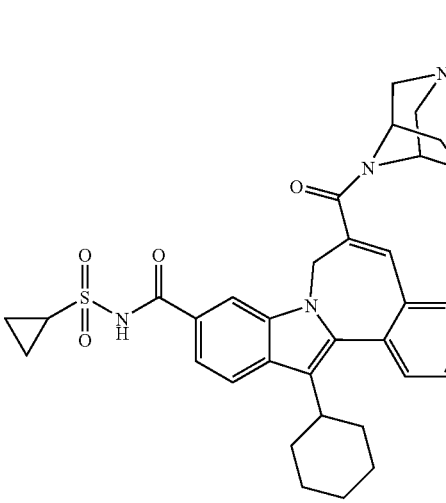 | B | B |

TABLE 1-continued
| Structure | IC$_{50}$ | EC$_{50}$ |
|---|---|---|
| 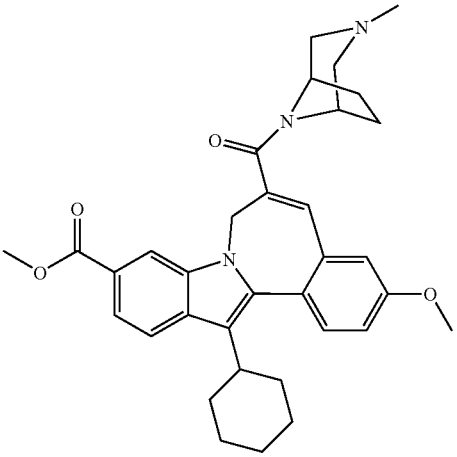 | A | A |
| 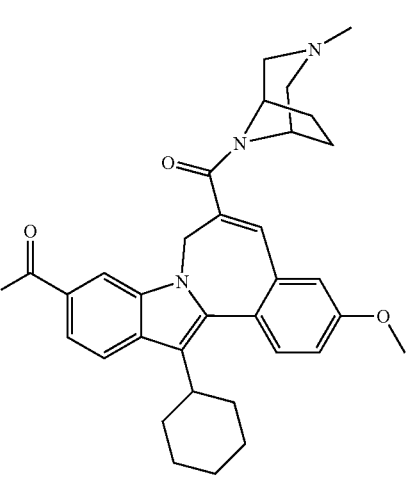 | B | B |
| 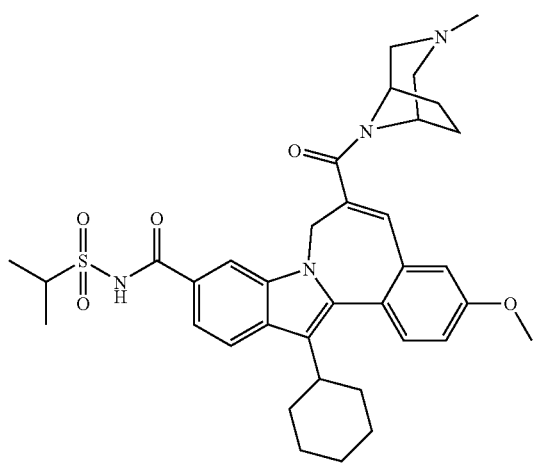 | B | B |

TABLE 1-continued

| Structure | IC$_{50}$ | EC$_{50}$ |
|---|---|---|
| 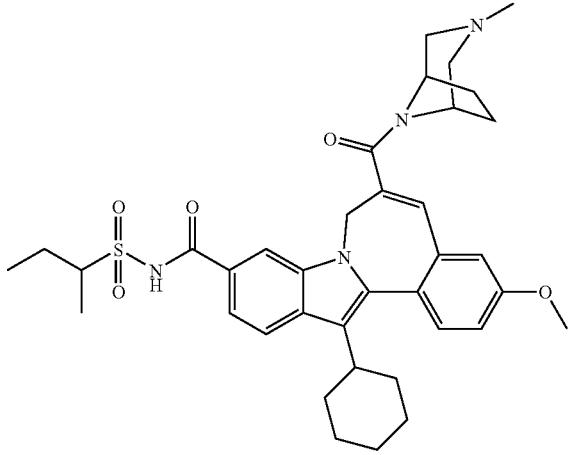 | B | B |

A > 0.5 µM; B 0.001 µM-0.5 µM; C < 0.02 µM but an exact value was not determined; IC$_{50}$ values were determined using the preincubation protocol. EC50 values were determined using the FRET assay.

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound of formula I or a pharmaceutically acceptable salt thereof.

Another aspect of the invention is a method of inhibiting the function of the HCV NS5B protein comprising contacting the HCV NS5B protein with a compound of formula I or a pharmaceutically acceptable salt thereof.

Another aspect of the invention is a method of treating an HCV infection in a patient comprising administering to the patient a therapeutically effective amount of a compound or a pharmaceutically acceptable salt thereof. Another aspect of the invention is a method of inhibiting the function of the HCV replicon. Another aspect of the invention is a method of inhibiting the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgment.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Type of Inhibitor or Target | Source Company |
| --- | --- | --- |
| Omega IFN | IFN-ω | Intarcia Therapeutics |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon-α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/SciClone Pharmaceuticals Inc, San Mateo, CA |
| Levovirin | IMPDH inhibitor | Ribapharm Inc., Costa Mesa, CA |
| Viramidine | Ribavirin Prodrug | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | Schering-Plough Corporation, Kenilworth, NJ |

TABLE 2-continued

| Brand Name | Type of Inhibitor or Target | Source Company |
|---|---|---|
| Zadazim | Immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| Batabulin (T67) | β-tubulin inhibitor | Tularik Inc., South San Francisco, CA |
| Merimepodib (VX-497) | IMPDH inhibitor | Vertex Pharmaceuticals Inc., Cambridge, MA |
| Telaprevir (VX-950, LY-570310) | NS3 serine protease inhibitor | Vertex Pharmaceuticals Inc., Cambridge, MA/ Eli Lilly and Co. Inc., Indianapolis, IN |
| Omniferon | natural IFN-α | Viragen Inc., Plantation, FL |
| XTL-6865 (XTL-002) | monoclonal antibody | XTL Biopharmaceuticals Ltd., Rehovot, Isreal |
| HCV-796 | NS5B Replicase Inhibitor | Wyeth/Viropharma |
| NM-283 | NS5B Replicase Inhibitor | Idenix/Novartis |
| GL-59728 | NS5B Replicase Inhibitor | Gene Labs/Novartis |
| GL-60667 | NS5B Replicase Inhibitor | Gene Labs/Novartis |
| 2'C MeA | NS5B Replicase Inhibitor | Gilead |
| PSI 6130 | NS5B Replicase Inhibitor | Roche |
| R1626 | NS5B Replicase Inhibitor | Roche |
| SCH 503034 | serine protease inhibitor | Schering Plough |
| NIM811 | Cyclophilin Inhibitor | Novartis |
| Suvus | Methylene blue | Bioenvision |
| Multiferon | Long lasting IFN | Viragen/Valentis |
| Actilon (CPG10101) | TLR9 agonist | Coley |
| Interferon-β | Interferon-β-1a | Serono |
| Zadaxin | Immunomodulator | Sciclone |
| Pyrazolopyrimidine compounds and salts From WO 2005047288 | HCV Inhibitors | Arrow Therapeutics Ltd. |
| 2'C Methyl adenosine | NS5B Replicase Inhibitor | Merck |
| GS-9132 (ACH-806) | HCV Inhibitor | Achillion/Gilead |

DESCRIPTION OF SPECIFIC EMBODIMENTS

Analytical LCMS data for most of the following intermediates and examples were acquired using the following columns and conditions. Stop time: Gradient time+1 minute; Starting conc: 0% B unless otherwise noted; Eluent A: 5% $CH_3CN/95\%$ $H_2O$ with 10 mM $NH_4OAc$ (for columns A, D and E); 10% $MeOH/90\%$ $H_2O$ with 0.1% TFA (for columns B and C); Eluent B: 95% $CH_3CN/5\%$ $H_2O$ with 10 mM $NH_4OAc$ (for columns A, D and E); 90% $MeOH/10\%$ $H_2O$ with 0.1% TFA (for columns B and C); Column A: Phenomenex 10μ 4.6×50 mm C18; Column B: Phenomenex C18 10μ 3.0×50 mm; Column C: Phenomenex 4.6×50 mm C18 10μ; Column D: Phenomenex Lina C18 5μ 3.0×50 mm; Column E: Phenomenex 5μ 4.6×50 mm C18. Preparative HPLC data. Gradient: Linear over 20 min. unless otherwise noted; Starting conc: 15% B unless otherwise noted; Ending conc: 100% B; Eluent A: 5% $CH_3CN/95\%$ $H_2O$ with 10 mM $NH_4OAc$; Eluent B: 95% $CH_3CN/5\%$ $H_2O$ with 10 mM $NH_4OAc$; Column: Sunfire Prep $C_{18}$ OBD 5μ 30×100 mm.

Intermediate 1

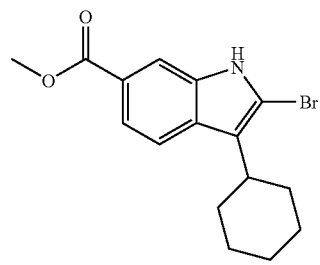

1H-Indole-6-carboxylic acid, 2-bromo-3-cyclohexyl-, methyl ester. Freshly recrystallized pyridinium tribromide (recrystallization from hot AcOH (5 mL per 1 g), rinsed with cold AcOH and dried under high vacuum over KOH) was added in portions (over 10 min.) to a stirring solution of methyl 3-cyclohexyl-1H-indole-6-carboxylate (60 g, 233 mmol) (prepared using procedures describe in WO2004/065367) in $CHCl_3/THF$ (1:1, 1.25 L) at 2o C. The reaction solution was stirred at 0-5° C. for 2.5 h, and washed with sat. aq. $NaHSO_3$ (1 L), 1 N HCl (1 L) and brine (1 L). The organic layer was dried ($MgSO_4$) and concentrated. The resulting red oil was diluted with $Et_2O$ and concentrated. The resulting pink solid was dissolved into $Et_2O$ (200 mL) treated with hexanes (300 mL) and partially concentrated. The solids were collected by filtration and rinsed with hexanes. The mother liquor was concentrated to dryness and the procedure repeated. The solids were combined to yield 1H-indole-6-carboxylic acid, 2-bromo-3-cyclohexyl-, methyl ester (64 g, 190 mmol, 82%) as a fluffy pink solid, which was used without further purification. 1HNMR (300 MHz, $CDCl_3$) δ 8.47 (br s, 1H), 8.03 (d, J=1.4 Hz, 1H), 7.74 (dd, J=1.4, 8.8 Hz, 1H), 7.69 (d, J=8.8 Hz, 1H), 3.92 (s, 3H), 2.82 (tt, J=3.7, 11.7 Hz, 1H), 1.98-1.72 (m, 7H), 1.50-1.27 (m, 3H). 13CNMR (75 MHz, CDCl3) δ 168.2, 135.6, 130.2, 123.1, 120.8, 120.3, 118.7, 112.8, 110.7, 52.1, 37.0, 32.2(2), 27.0 (2), 26.1. LCMS: m/e 334 (M–H)⁻, ret time 3.34 min, column A, 4 minute gradient.

Intermediate 2

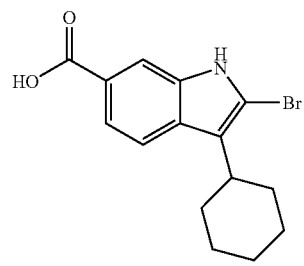

1H-Indole-6-carboxylic acid, 2-bromo-3-cyclohexyl-. A solution of methyl 2-bromo-3-cyclohexyl-1H-indole-6-carboxylate (20 g, 60 mmol) and LiOH (3.8 g, 160 mmol) in $MeOH/THF/H_2O$ (1:1:1, 300 mL) was heated at 90° C. for 2 h. The reaction mixture was cooled in an ice/$H_2O$ bath, neutralized with 1M HCl (~160 mL) diluted with $H_2O$ (250 mL) and stirred for 1 h at rt. The precipitates were collected by filtration rinse with $H_2O$ and dried to yield 1H-indole-6- carboxylic acid, 2-bromo-3-cyclohexyl- (quant.) which was used without further purification.

An alternative procedure that can by used to provide 1H-indole-6-carboxylic acid, 2-bromo-3-cyclohexyl- is described below:

A solution of methyl 2-bromo-3-cyclohexyl-1H-indole-6-carboxylate (117 g, 349 mmol) and LiOH.H$_2$O (26.4 g, 629 mmol) in MeOH/THF/H2O (1:1:1, 1.8 L) was heated at reflux for 3 h. The reaction mixture was cooled in an ice/H$_2$O bath to 2° C., neutralized with 1M HCl (~650 mL) (added at such a rate that temperature did not exceed 5° C.), diluted with H2O (1 L) and stirred while warming to ambient temperature. The precipitates were collected by filtration rinsed with H$_2$O and dried to yield the mono THF solvate of 1H-indole-6-carboxylic acid, 2-bromo-3-cyclohexyl- (135.5 g, 345 mmol, 99%) as a yellow solid, which was used without further purification. $^1$HNMR (300 MHz, CDCl$_3$) δ 11.01 (br s, 1H), 8.77 (s, 1H), 8.07 (d, J=1.5 Hz, 1H), 7.82 (dd, J=1.5, 8.8 Hz, 1H), 7.72 (d, J=8.8 Hz, 1H), 3.84-3.74 (m, 4H), 2.89 (m, 1H), 1.98-1.72 (m, 11H), 1.50-1.24 (m, 3H). 13CNMR (75 MHz, CDCl3) δ 172.7, 135.5, 130.7, 122.3, 120.9(2), 118.8, 113.3, 111.1, 67.9(2), 37.0, 32.2(2), 27.0 (2), 26.1, 25.5(2). LCMS: m/e 320 (M–H)$^-$, ret time 2.21 min, column A, 4 minute gradient.

Intermediate 3

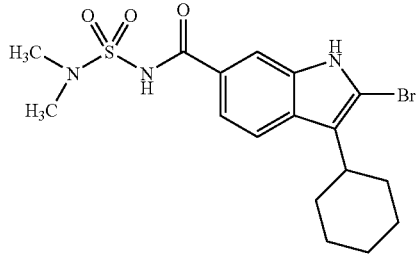

1H-Indole-6-carboxamide, 2-bromo-3-cyclohexyl-N-[(dimethylamino)sulfonyl]-. 1,1'-Carbonyldiimidazole (1.17 g, 7.2 mmol) was added to a stirred solution of 2-bromo-3-cyclohexyl-1H-indole-6-carboxylic acid (2.03 g, 6.3 mmol) in THF (6 mL) at 22° C. The evolution of CO$_2$ was instantaneous and when it slowed the solution was heated at 50° C. for 1 hr and then cooled to 22° C. N,N-Dimethylsulfamide (0.94 g, 7.56 mmol) was added followed by the dropwise addition of a solution of DBU (1.34 g, 8.8 mmol) in THF (4 mL). Stirring was continued for 24 hr. The mixture was partitioned between ethyl acetate and dilute HCl. The ethyl acetate layer was washed with water followed by brine and dried over Na$_2$SO$_4$. The extract was concentrated to dryness to leave the title product as a pale yellow friable foam, (2.0 g, 74%, >90% purity, estimated from NMR). $^1$H NMR (300 MHz, DMSO-D6) δ ppm 1.28-1.49 (m, 3H) 1.59-2.04 (m, 7H) 2.74-2.82 (m, 1H) 2.88 (s, 6H) 7.57 (dd, J=8.42, 1.46 Hz, 1H) 7.74 (d, J=8.78 Hz, 1H) 7.91 (s, 1H) 11.71 (s, 1H) 12.08 (s, 1H).

An alternative method for the preparation of 1H-indole-6-carboxamide, 2-bromo-3-cyclohexyl-N-[(dimethylamino)sulfonyl]- is described below.

To a 1 L four necked round bottom flask equipped with a mechanical stirrer, a temperature controller, a N2 inlet, and a condenser, under N2, was added 2-bromo-3-cyclohexyl-1H-indole-6-carboxylic acid (102.0 g, 0.259 mol) and dry THF (300 mL). After stirring for 10 min, CDI (50.3 g, 0.31 mol) was added portion wise. The reaction mixture was then heated to 50 oC for 2 h. After cooling to 30 oC, N,N-dimethylaminosulfonamide (41.7 g, 0.336 mol) was added in one portion followed by addition of DBU (54.1 mL, 0.362 mol) drop wise over a period of 1 h. The reaction mixture was then stirred at rt for 20 h. The solvent was removed in vacuo and the residue was partitioned between EtOAc and 1 N HCl (1:1, 2 L). The organic layer was separated and the aqueous layer was extracted with EtOAc (500 mL). The combined organic layers were washed with brine (1.5 L) and dried over MgSO4. The solution was filtered and concentrated in vacuo to give the crude product (111.0 g). The crude product was suspended in EtOAc (400 mL) at 60 oC. To the suspension was added heptane (2 L) slowly. The resulting suspension was stirred and cooled to 0 oC. It was then filtered. The filter cake was rinsed with small amount of heptane and house vacuum air dried for 2 days. The product was collected as a white solid (92.0 g, 83%). $^1$H NMR (MeOD, 300 MHz) δ 7.89 (s, H), 7.77 (d, J=8.4 Hz, 1H), 7.55 (dd, J=8.4 and 1.8 Hz, 1H), 3.01 (s, 6H), 2.73-2.95 (m, 1H), 1.81-2.05 (m, 8H), 1.39-1.50 (m, 2H); m/z 429 (M+H)+.

Intermediate 4

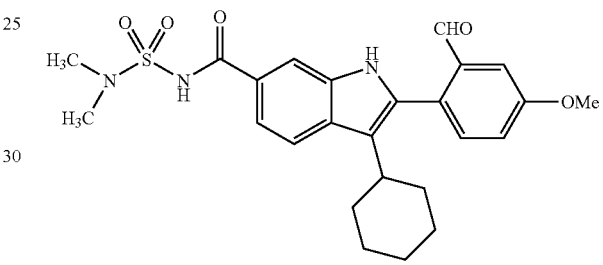

1H-Indole-6-carboxamide, 3-cyclohexyl-N-[(dimethylamino)sulfonyl]-2-(2-formyl-4-methoxyphenyl)-. A mixture of the 2-Bromo-3-cyclohexyl-N-[(dimethylamino)sulfonyl]-1H-indole-6-carboxamide (4.28 g, 0.01 mol), 4-methoxy-2-formylphenyl boronic acid (2.7 g, 0.015 mol), 2-dicyclohexylphosphino-2',6'-dimethoxy-biphenyl (41 mg, 0.0001 mol), palladium acetate (11.2 mg), and finely ground potassium carbonate (4.24 g, 0.02 mol) in toluene (30 mL) was stirred under reflux and under nitrogen for 30 min, at which time LC/MS analysis showed the reaction to be complete. The reaction mixture was then diluted with ethyl acetate and water, and then acidified with an excess of dilute HCl. The ethyl acetate layer was then collected and washed with dilute HCl, water and brine. The organic solution was then dried (magnesium sulfate), filtered and concentrated to give a gum. The gum was diluted with hexanes (250 ml) and ethyl acetate (25 mL), and the mixture was stirred for 20 hr at 22° C. during which time the product was transformed into a bright yellow granular solid (4.8 g) which was used directly without further purification.

An alternative procedure for the preparation of 1H-indole-6-carboxamide, 3-cyclohexyl-N-[(dimethylamino)sulfonyl]-2-(2-formyl-4-methoxyphenyl)- is provided below:

To a slurried solution of 2-bromo-3-cyclohexyl-N-[(dimethylamino)sulfonyl]-indole-6-carboxamide (54.0 g, 126 mmol), 4-methoxy-2-formylphenylboronic acid (29.5 g, 164 mmol) and LiCl (13.3 g, 315 mmol) in EtOH/toluene (1:1, 1 L) was added a solution of Na$_2$CO$_3$ (40.1 g, 379 mmol) in water (380 mL). The reaction mixture was stirred 10 min. and then Pd(PPh3)$_4$ (11.3 g, 10.0 mmol) was added. The reaction solution was flushed with nitrogen and heated at 70° C. (internal monitoring) overnight and then cooled to rt. The reaction was diluted with EtOAc (1 L) and EtOH (100 mL), washed carefully with 1N aqueous HCl (1 L) and brine (500 mL), dried (MgSO4), filtered and concentrated. The residual solids were stirred with Et2O (600 mL) for 1 h and collected by filtration to yield 1H-indole-6-carboxamide, 3-cyclohexyl-N-[(dimethylamino)sulfonyl]-2-(2-formyl-4-methoxyphenyl)- (52.8 g, 109 mmol, 87%) as a yellow powder which was used without further purification. 1HNMR (300 MHz, d6-DMSO) δ 11.66 (s, 1H), 8.17 (s, 1H), 7.75 (d, J=8.4 Hz, 1H), 7.74 (d, J=8.4 Hz, 1H), 7.59 (dd, J=1.4, 8.4 Hz, 1H), 7.23-7.16 (m, 2H), 7.08 (dd, J=2.6, 8.4 Hz, 1H), 6.54 (d, J=8.8 Hz, 1H), 3.86 (s, 3H), 3.22-3.08 (m, 1H), 2.91 (s, 6H), 2.00-1.74 (m, 7H), 1.60-1.38 (m, 3H). 13CNMR (75 MHz, CDCl3) δ 165.7, 158.8, 147.2, 139.1, 134.3, 132.0, 123.4, 122.0, 119.2, 118.2, 114.8, 112.3, 110.4, 109.8, 79.6, 45.9, 37.2(2), 34.7, 32.0(2), 25.9 (2), 24.9. LCMS: m/e 482 (M−H)⁻, ret time 2.56 min, column A, 4 minute gradient.

Intermediate 5

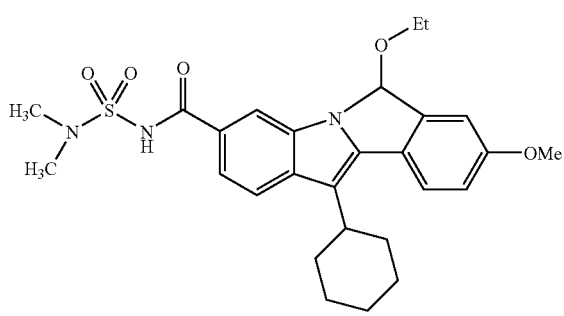

6H-Isoindolo[2,1-a]indole-3-carboxamide, 11-cyclohexyl-N-[(dimethylamino)sulfonyl]-6-ethoxy-8-methoxy-. To a 5 L four necked round bottom flask equipped with a temperature controller, a condenser, a N2 inlet and a mechanical stirrer, was charged toluene (900 mL), EtOH (900 mL), 2-bromo-3-cyclohexyl-N—(N,N-dimethylsulfamoyl)-1H-indole-6-carboxamide (90 g, 0.21 mol), 2-formyl-4-methoxyphenylboronic acid (49.2 g, 0.273 mol) and LiCl (22.1 g, 0.525 mol). The resulting solution was bubbled with N₂ for 15 mins. A solution of Na₂CO₃ (66.8 g, 0.63 mol) in H₂O (675 mL) was added and the reaction mixture was bubbled with N₂ for another (10 mins). Pd(PPh₃)₄ (7.0 g, 6.3 mmol) was added and the reaction mixture was heated to 70° C. for 20 h. After cooling to 35° C., a solution of 1 N HCl (1.5 L) was added slowly. The resulting mixture was transferred to a 6 L separatory funnel and extracted with EtOAc (2×1.5 L). The combined organic extracts were washed with brine (2 L), dried over MgSO4, filtered and concentrated in vacuo to give a yellow solid, which was triturated with 20% EtOAc in hexane (450 mL, 50° C. to 0° C.) to give 3-cyclohexyl-N—(N,N-dimethylsulfamoyl)-2-(2-formyl-4-methoxyphenyl)-1H-indole-6-carboxamide (65.9 g) as a yellow solid. HPLC purity, 98%.

The mother liquid from the trituration was concentrated in vacuo. The residue was refluxed with EtOH (50 mL) for 3 h. The solution was then cooled to 0° C. The precipitates were filtered and washed with cooled TBME (5° C.) (20 mL). The filter cake was house vacuum air dried to give a further quantity of the title compound as a white solid (16.0 g). HPLC purity, 99%. ¹H NMR (CDCl3, 300 MHz) δ 8.75 (s, 1H), 7.96 (s, 1H), 7.73 (d, J=8.4 Hz, 1H), 7.67 (d, J=8.4 Hz, 1H), 7.45 (dd, J=8.4 and 1.4 Hz, 1H), 7.09 (d, J=2.2 Hz, 1H), 6.98 (dd, J=8.4 and 2.2 Hz, 1H), 6.50 (s, 1H), 3.86 (s, 3H), 3.05 (s, 6H), 2.92-3.13 (m, 3H), 1.85-1.93 (m, 7H), 1.40-1.42 (m, 3H), 1.05 (t, J=7.1 Hz, 3H). m/z 512 (M+H)+.

Intermediate 6

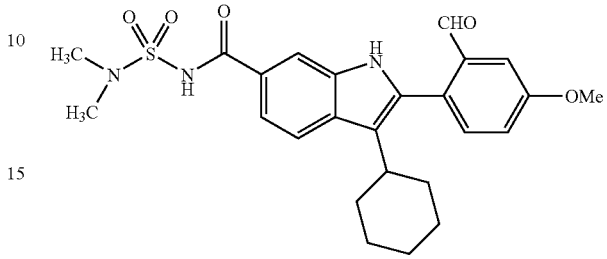

1H-indole-6-carboxamide, 3-cyclohexyl-N-[(dimethylamino)sulfonyl]-2-(2-formyl-4-methoxyphenyl)-. 11-cyclohexyl-N—(N,N-dimethylsulfamoyl)-6-ethoxy-8-methoxy-6H-isoindolo[2,1-a]indole-3-carboxamide was dissolved in THF (75 mL). To the solution was added a solution of 2 N HCl (300 mL). The mixture was vigorously stirred under N2 at rt for 16 h. The resulting suspension was filtered and washed with cooled TBME (2×30 mL). the filer cake was vacuum air dried overnight to give the title compound as a yellow solid. HPLC purity, 99% ¹H NMR (DMSO-d6, 300 MHz) δ 11.65 (s, 1H), 8.16 (s, 1H), 7.76 (d, J=5.9 Hz, 1H), 7.73 (d, J=5.9 Hz, 1H), 7.58 (dd, J=8.5 and 1.5 Hz, 1H), 7.17-7.20 (m, 2H), 7.08 (dd, J=8.5 and 1.4 Hz, 1H), 6.55 (d, J=8.6 Hz, 1H), 3.86 (s, 3H), 3.14-3.18 (m, 1H), 2.91 (s, 6H), 1.75-1.99 (m, 7H), 1.48-1.60 (m, 3H); m/z 484 (M+H)+.

Intermediate 7

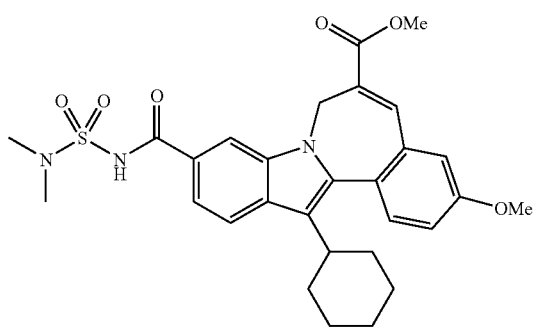

7H-Indolo[2,1-a][2]benzazepine-6-carboxylic acid, 13-cyclohexyl-10-[[[(dimethylamino)sulfonyl]amino]carbonyl]-3-methoxy-, methyl ester. A mixture of the 3-cyclohexyl-N—(N,N-dimethylsulfamoyl)-2-(2-formyl-4-methoxyphenyl)-1H-indole-6-carboxamide (4.8 g, 0.01 mol), methyl 2-(dimethoxyphosphoryl)acrylate (9.7 g, 0.02 mol) and cesium carbonate (7.1 g, 0.02 mol) in DMF (28 mL) was stirred for 20 hr at an oil bath temperature of 55° C. The mixture was poured into ice-water and acidified with dilute HCl to precipitate the crude product. The solid was collected, dried and flash chromatographed on SiO₂ (110 g) using an ethyl acetate and methylene chloride (1:10) solution containing 2% acetic acid. Homogeneous fractions were combined and evaporated to afford the title compound as a pale yellow solid (3.9 g, 71% yield). MS: 552 (M=H+).

An alternate procedure for the preparation of 7H-indolo[2,1-a][2]benzazepine-6-carboxylic acid, 13-cyclohexyl-10-[[[(dimethylamino)sulfonyl]amino]carbonyl]-3-methoxy-, methyl ester is provided below.

A solution of 11-cyclohexyl-N-[(dimethylamino)sulfonyl]-6-hydroxy-8-methoxy-6H-isoindolo[2,1-a]indole-3-carboxamide (cyclic hemiaminal) (63.0 g, 130 mmol), methyl 2-(dimethoxyphosphoryl)acrylate (60 g, 261 mmol), cesium carbonate (106 g, 326 mmol) in DMF (400 mL) was heated at 60° C. (bath temp) for 4.5 h. Additional methyl 2-(dimethoxyphosphoryl)acrylate (15 g, 65 mmol) and cesium carbonate (21.2 g, 65 mmol) were added and the reaction was heated at 60° C. overnight then and cooled to rt. The stirring reaction mixture was diluted with H$_2$O (1 L), slowly neutralized with 1N aqueous HCl (800 mL), stirred 3 h, and then the precipitates were collected by filtration. The solids were triturated with Et2O (800 mL) and dried to yield methyl 7H-indolo[2,1-a][2]benzazepine-6-carboxylic acid, 13-cyclohexyl-10-[[[(dimethylamino)sulfonyl]amino]carbonyl]-3-methoxy-, methyl ester (70.2 g, 127 mmol, 98%) as a yellow solid which was used without further purification. 1HNMR (300 MHz, CDCl3) δ 8.67 (s, 1H), 8.09 (s, 1H), 7.86 (d, J=8.4 Hz, 1H), 7.80 (s, 1H), 7.50 (d, J=8.4 Hz, 1H), 7.42 (d, J=8.8 Hz, 1H), 7.08 (dd, J=2.6, 8.8 Hz, 1H), 6.98 (d, J=2.6 Hz, 1H), 5.75-5.51 (m, 1H), 4.29-4.01 (m, 1H), 3.89 (s, 3H), 3.82 (s, 3H), 3.05 (s, 6H), 2.87-2.73 (m, 1H), 2.11-1.12 (m, 10H). LCMS: m/e 550 (M−H)−, ret time 3.21 min, column A, 4 minute gradient.

Intermediate 8

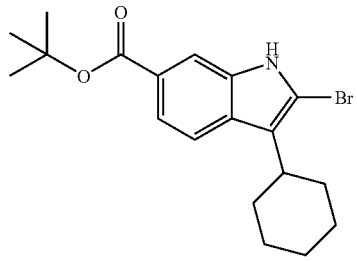

1H-Indole-6-carboxylic acid, 2-bromo-3-cyclohexyl-, 1,1-dimethylethyl ester. To a mechanically stirred solution of 2-bromo-3-cyclohexyl-1H-indole-6-carboxylic acid (80 g, 0.24 m) in dry methylene dichloride (1.2 L) and THF (100 mL) were added activated molecular sieves (4A, 80 g) and silver carbonate (275 g, 0.99 m). The reaction mixture was cooled to 0° C. and t-Butyl bromide (142 g, 1.04 m) was added drop wise. The mixture was stirred overnight at rt and monitored by TLC (Hexane-Ethyl acetate 80:20, R$_f$ (Product) =0.7). If any bromo acid was left unconverted a further 10% of silver carbonate was added and stirring was continued for an addition 2-4 h. On completion, the reaction mixture was filtered through a thin bed of celite. The filtrand was washed with methylene dichloride (500 mL). The combined filtrates were concentrated in-vacuo, and the crude product thus obtained was purified by silica gel chromatography: (230-400 mesh, eluted with a gradient of ethyl acetate in pet ether 0-2%). Homogeneous fractions were combined and evaporated under reduced pressure to give 80 g (85%) of the title compound. HPLC: 90.1% (RT=6.56 min), Column: C18 BDS, (50×4.6 mm), Mobile Phase Gradient of 0.1% TFA in water: ACN (30→100→30), Flow rate 0.8 mL/min. LCMS: 99.8% (RT=4.44 min), Column: Geneis, C18 50×4.6 mm Mobile Phase Gradient of 0.1% Formic acid in water: ACN (70→95→70), Flow rate: 0.8 mL/min; M−1=376.5; $^1$H NMR CDCl$_3$) (400 MHz) δ 1.37-1.40 (m, 3H, cyc.Hexyl), 1.62 (s, 9H, t-Bu), 1.80-1.94 (two sets of m, 3H, & 4H respectively, cyc.Hexyl part), 2.81 (m, 1H, CH of cyc.Hexyl-benzylic), 7.70-7.75 (m, 2H, Indole-H$_{4\&5}$), 8.04 (s, 1H, Indole-H$_7$), 8.52 (s, 1H, Indole-NH).

Intermediate 9

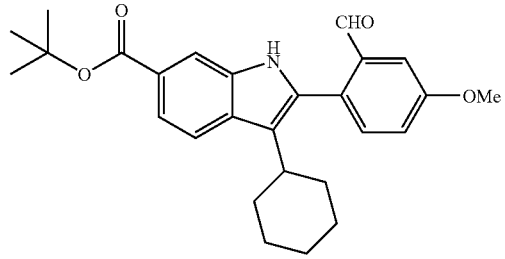

1H-Indole-6-carboxylic acid, 3-cyclohexyl-2-(2-formyl-4-methoxyphenyl)-, 1,1-dimethylethyl ester. tert-Butyl 2-bromo-3-cyclohexyl-1H-indole-6-carboxylate (72 g, 0.19 m) was dissolved in a 1:1 mixture of toluene and ethanol (720 mL) and degasified. LiCl (23.9 g, 0.51 m) was then added, followed by sodium carbonate (720 mL, 1.0 M solution degasified separately,) and Pd-tetrakis (13.1 g, 0.011 m). After stirring for 0.25 h, 2-formyl-4-methoxyphenylboronic acid (41.1 g, 0.22 m) was added and the reaction mixture was heated to 85° C. for 4 h. The reaction was then monitored by TLC, (Hexane-Ethyl acetate 80:20, R$_f$ (Product)=0.55). On completion, the reaction mixture was cooled to rt and water (1.0 L) was added followed by ethyl acetate (1.0 L). The organic layer was washed with brine, and dried and concentrated under vacuum to afford the title compound as a yellow solid. Yield 75 g (74%). HPLC: 99.7% (RT=6.30 min), Column: C18 BDS (4.6×50 mm), SC-307, Mobile Phase: Gradient of 0.1% TFA in water: ACN (30→100→30), Flow rate 0.8 mL/min. LCMS: 98.0% (RT=5.28 min), Column: Geneis, C18 (50×4.6 mm), Mobile Phase: Gradient of 0.1% Formic acid in water: ACN (70→95→70), Flow rate: 0.8 mL/min; M−1=432.2; $^1$H NMR (DMSO-d$_6$) (400 MHz) δ 1.40-1.48 (m, 3H, cyc.Hexyl), 1.57 (s, 9H, t-Bu), 1.84-1.90 (m, 7H, cyc.Hexyl part), 3.09 (m, 1H, CH of cyc.Hexyl-benzylic), 3.84 (s, 3H, OCH$_3$), 6.55 (d, J=4 Hz, 1H, aryl H$_2$,), 7.06 (d, 1H, aryl H$_3$,), 7.08 (s, 1H, aryl H$_6$,), 7.23 (d, 1H, Indole-H$_5$), 7.53 (d, J=8 Hz, 1H, Indole-H$_4$), 7.70-7.75 (m, 2H, NH+Indole-H$_7$), 8.06 (s, 1H, CHO).

Intermediate 10

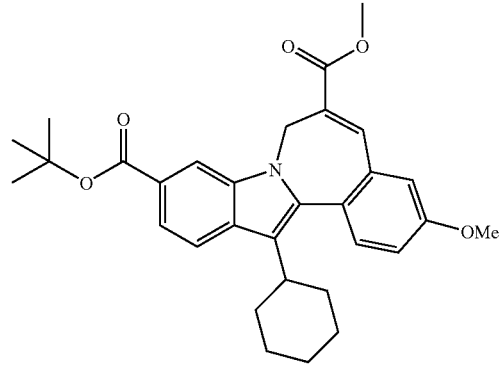

7H-Indolo[2,1-a][2]benzazepine-6,10-dicarboxylic acid, 13-cyclohexyl-, 10-(1,1-dimethylethyl) 6-methyl ester. tert-Butyl 3-cyclohexyl-2-(2-formyl-4-methoxyphenyl)-1H-indole-6-carboxylate (62.5 g, 0.144 m) was dissolved in dry DMF (1.2 L) and stirred mechanically. Cesium carbonate (84 g, 0.17 m) and methyl 2-(dimethoxyphosphoryl)acrylate (65-70% GC pure, 56.2 g, 0.18 m) were then added and the reaction mixture was heated to 65° C. for 4 h, and the reaction was monitored by TLC (Hexane-Ethyl acetate 80:20, $R_f$ (Product)=0.7). On completion, the mixture was cooled to rt, then quenched with water (1.0 L). A yellow solid precipitated, which was collected by filtration and air dried. This material was then slurried in methanol, filtered, and dried under vacuum to give the product as a yellow powder, (70 g, 90%). HPLC: 99.1% (RT=6.45 min), Column: C18 BDS (4.6×50 mm), Mobile Phase: Gradient of 0.1% TFA in water: ACN (30→100→30), Flow rate 0.8 mL/min. LCMS: 100% (RT=7.00 min), Column: Geneis, C18 (50×4.6 mm), Mobile Phase: Gradient of 0.1% Formic acid in water: ACN (70→95→70), Flow rate: 0.8 mL/min; M+1=502.2; $^1$H NMR (CDCl$_3$) (400 MHz) δ 1.10-1.30 (m, 3H, cyc.Hexyl), 1.64 (s, 9H, t-Bu), 1.77-2.07 (m, 7H, cyc.Hexyl part), 2.80 (m, 1H, CH of cyc.Hexyl-benzylic), 3.84 (s, 3H, OCH$_3$), 3.93 (s, 3H, COOCH$_3$), 4.15 & 5.65 (two br. peak., 1H each, allylic CH$_2$), 6.95 (s, 1H, aryl H$_{6'}$), 7.01 (d, 1H, aryl H$_{2'}$), 7.53 (d, J=8 Hz, 1H, aryl H$_{3'}$), 7.70 (d, J=4 Hz, 1H, Indole-H$_5$), 7.84 (s+d, 2H, olefinic H+Indole-H$_4$), 8.24 (s, 1H, indole-H$_7$); $^{13}$C NMR (CDCl$_3$) (100.0 MHz) δ 166.92, 165.71, 158.96, 142.28, 136.47, 13.50, 134.61, 132.43, 132.01, 129.73, 124.78, 124.68, 120.33, 119.39, 119.04, 115.62, 115.05, 111.27, 80.27, 55.49, 52.50, 39.09, 36.81, 33.40, 28.38, 27.15, 26.28.

Intermediate 11

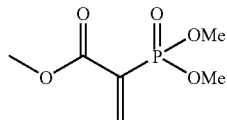

2-Propenoic acid, 2-(dimethoxyphosphinyl)-, methyl ester. To a 5 L four necked round bottom flask equipped with a mechanical stirrer, a condenser, a temperature controller and a N2 inlet, was charged paraformaldehyde (40.5 g, 1.35 mol), MeOH (2 L) and piperidine (2 mL). The reaction mixture was heated to reflux under N2 for 3 h. After cooling to 50 oC, 2-(dimethoxyphosphoryl)acetate (150 g, 0.824 mol) was added in one portion. The reaction mixture was continued to reflux for 18 h. After cooling to rt, the reaction solution was concentrated in vacuo to give a clear colorless oil. The above oil was dissolved in dry toluene (1 L) in a 3 L four necked round bottom flask equipped a temperature controller, a N$_2$ inlet, a magnetic stirrer and a Dean-Stark apparatus. To the solution was added TsOH.H$_2$O (5.2 g). The reaction mixture was then refluxed azeotropically to remove methanol for 18 h. After cooling to rt, the solution was concentrated in vacuo to give a yellow oil which was vacuum distilled at 150-155 oC/0.2 mmHg to afford the product as a colorless oil (135.0 g). Purity, 90% based on $^1$H NMR. $^1$H NMR (CDCl3, 300 MHz) δ 7.0 (dd, J=42.4 and 1.5 Hz, 1H), 6.73 (dd, J=20.5 and 1.8 Hz, 1H), 3.80 (s, 6H), 3.76 (s, 3H).

Intermediate 12

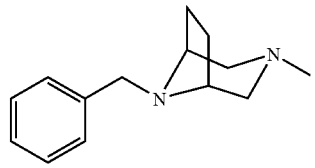

3,8-Diazabicyclo[3.2.1]octane, 3-methyl-8-(phenylmethyl)-. Cis-1-Benzyl-2,5-bis(chloromethyl)pyrrolidine hydrochloride (37.5 g, 0.13 mol) (Prepared as described in Published PCT patent application WO200232902) was suspended in CH$_3$CN (900 mL) in a 3-neck 5 L round bottom flask fitted with mechanical stirrer, reflux condenser, and thermometer. The stirred suspension was warmed to 50° C., NaHCO$_3$ (97 g, 1.1 mol) was added, and the suspension was warmed to 70° C. NaI (50 g, 0.33 mol) was added and stirred at 70° C. for 5 min, at which point an addition funnel was affixed atop the condenser. To the addition funnel was added 48 mL of 40% aqueous MeNH$_2$ (0.55 mol) in 850 mL of CH$_3$CN, and this solution was added dropwise (rate of addition maintained between 10-15 ml/min). The addition was complete after 75 min, at which point the reaction was cooled to rt., the solids filtered off, and the solvent concentrated to ~800 mL. The reaction was poured into EtOAc (800 mL) and washed with 1 N NaOH (2×100 mL). The aqueous phase was re-extracted with EtOAc (2×100 mL), the combined organic phases were dried over Na$_2$SO$_4$ and concentrated. The resulting residue was introduced on to silica gel (620 g) and eluted with 2.8% MeOH/0.4% conc. NH$_4$OH in CHCl$_3$ (6 L total). Pure fractions were collected from 2 L to 4 L. Concentration yielded 8.76 g (32% yield) of the title compound as a brown oil. $^1$H NMR (400 MHz, CDCl3) δ ppm 1.79-1.87 (m, 2H) 1.92-1.99 (m, 2H) 2.23 (s, 3H) 2.27-2.37 (m, 2H) 2.54-2.63 (m, 2H) 3.10 (s, 2H) 3.52 (s, 2H) 7.20-7.26 (m, 1H) 7.30 (t, J=7.30 Hz, 2H) 7.36-7.42 (m, 2H). LC method: Solvent A=10% MeOH/90% H2O/0.1% TFA, Solvent B=90% MeOH/10% H2O/0.1% TFA, Start % B=0%, Final % B=100, Flow Rate=4 ml/min, Gradient time=2 min, Run time=3 min, Column: Phenomenex-Luna 10 □m C18 50 mm×3.0 mm, Rt=0.23 min; MS: (ES+) m/z (M+H)+=217.3. An additional 6.1 g of mixed fractions were obtained from the column (>80% pure by $^1$H NMR integration).

Intermediate 13

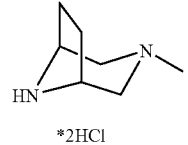

*2HCl 3,8-Diazabicyclo[3.2.1]octane, 3-methyl-, dihydrochloride. N-methyl-N-benzylbicyclodiamine, (14.22 g, 65.7 mMol) was dissolved in 650 ml of methanol and 17 ml of 12M aqueous hydrochloric acid was added. The solution was placed in a 2 L Parr bottle under nitrogen and 3.66 g of 20% palladium hydroxide on carbon added to the reaction. The mixture was placed on a Parr shaker under 60 psig of hydrogen for 17 hours. The reaction was judged complete by TLC analysis (Silica Gel plate eluted with a 10 parts by volume solution of 2M ammonia in methanol dissolved in 90 parts by volume of chloroform). The reaction was filtered through a plug of ceilite, which was then rinsed sequentially with water and methanol. The combined filtrates were concentrated in vacuuo and methanol and benzene added until a homogenous solution was obtained. 75 mL of 2.0M hydrochloric acid in diethyl ether was then added. Volatiles were removed from the product solution in vacuuo. A pale yellow solid was eventually obtained by repeated azetroping of water from the product solution using a methanol/benzene mixture. The solid product, 3-methyl-3,8-diazabicyclo[3.2.1]octane was dried in vacuuo overnight to obtain 11.98 g (91%) of a hygroscopic solid. The product was removed from the flask and bottled in a glove bag under nitrogen due to its hygroscopic nature. $^1$H NMR (500 MHz, DMSO-D6) δ ppm 1.96-2.14 (m, 2H) 2.34 (d, J=8.24 Hz, 2H) 2.66 (s, 3H) 3.46 (d, J=11.90 Hz, 2H) 3.58 (s, 3H, contains H2O) 4.17 (s, 2H) 9.92 (s, 1H) 10.21 (s, 1H) 11.39 (s, 1H); $^{13}$C NMR (126 MHz, DMSO-D6) δ ppm 24.04 (s, 1C) 43.49 (s, 1C) 52.50 (s, 1C) 54.47 (s, 1C).

Intermediate 14 and 15

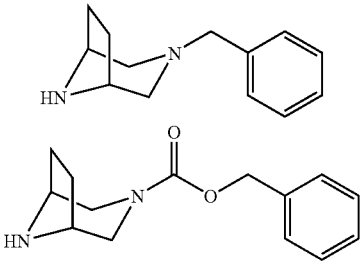

3,8-diazabicyclo[3.2.1]octane-3-carboxylic acid, phenylmethyl ester and 3-(phenylmethyl)-3,8-diazabicyclo[3.2.1]octane. Triethylamine (1.44 mL, 10.363 mmol) was added to a solution of 8-boc-3,8-diaza-bicyclo[3.2.1]ocatane (2.0 g, 9.421 mmol) in CH$_2$Cl$_2$ (20 mL), Benzyl chloroformate (1.46 mL, 10.363 mmol) was added dropwise at 0° C. and the reaction mixture was stirred at 0° C. for 0.5 hr, then allowed to warm to rt. and stirring was continued for 3 days. The reaction mixture was then quenched with water and acidified with 1N HCl solution. The organic layer was separated, washed with brine, dried (MgSO$_4$) and concentrated to give a colorless thick oil as the crude product. 70 mg of this material was then dissolved in 1,2-dichloroethane (2 mL) and TFA (0.5 mL) was added. The reaction mixture was stirred at rt. for 2 hr. The solvent and TFA were then evaporated to give a mixture of the two title compounds as a colorless thick oil.

Intermediate 16

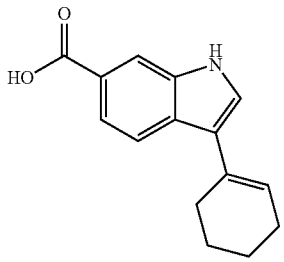

3-Cyclohexenyl-1H-indole-6-carboxylic acid. Cyclohexanone (96 mL, 0.926 mol) was added to a stirred solution of methyl indole-6-carboxylic acid (50.0 g, 0.335 mol) in methanol (920 mL) at 22° C. Methanolic sodium methoxide (416 mL of 25% w/w, 1.82 mol) was added in portions over 10 minutes. The mixture was stirred at reflux for 18 hours, cooled to room temperature, concentrated, diluted with cold water, and acidified with 36% HCl solution. The resulting precipitate was collected by filtration, washed with cold water, and dried over phosphorous pentoxide (0.1 mm) to provide the title compound as a tan colored solid (80.9 g, 97.5% yield).

Intermediate 17

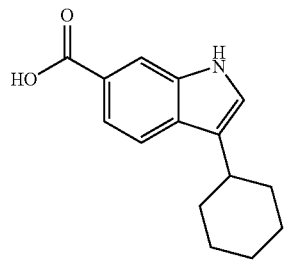

3-Cyclohexyl-1H-indole-6-carboxylic acid. 3-Cyclohexenyl-1H-indole-6-carboxylic acid (38 g) was added to a Parr bottle, followed by methanol (100 mL) and THF (100 mL). The bottle was flushed with argon and 10% palladium on carbon (1.2 g) was added. The flask was then evacuated and subsequently refilled with H$_2$ to a pressure of 55 psi, and the resultant mixture was shaken for 18 hours at RT. The catalyst was then removed by filtration through celite. Concentration of the filtrate provided the desired product as a pale purple solid (30.6 g, 79%). ESI-MS m/z 244 (MH+).

Intermediate 18

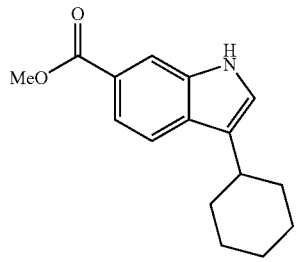

Methyl 3-cyclohexyl-1H-indole-6-carboxylate. Thionyl chloride (1 mL) was added to a stirred mixture of 3-cyclohexyl-1H-indole-6-carboxylic acid (30.4 g, 0.125 mol) in methanol (300 mL). The mixture was stirred at reflux for 18 hours, treated with decolorizing carbon, and filtered. The filtrate was concentrated to about 150 mL at which point crystallization occurred. The filtrate was cooled to room temperature and filtered. The solid was washed with cold methanol followed by diethyl ether to provide the desired product as a pale purple solid (22.2 g, 69% yield). ESI-MS m/z 258 (MH+); $^1$H NMR (300 MHz, CDCl$_3$.) δ 1.35 (m, 4H), 1.63 (s, 1H), 1.78 (m, 3H), 2.06 (d, J=8.05 Hz, 2H, 3.90 (m, 1H), 7.08 (d, J=1.83 Hz, 1H), 7.62 (s, 1H), 7.65 (s, 1H), 7.74 (d, J=1.46 Hz, 1H), 7.77 (d, J=1.46 Hz, 1H), 8.08 (s, 1H).

Intermediate 19

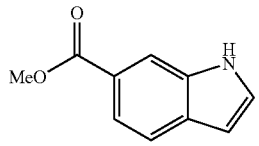

Methyl 1H-indole-6-carboxylate. An ethereal solution of diazomethane (620 mL) was added slowly to a cooled, (−15° C.) stirred suspension of 6-indole carboxylic acid (45 g, 0.27 mol.) in diethyl ether (250 mL). Upon addition, the reaction mixture was stirred for a further 1 h at −15° C., after which the reaction was quenched by the slow addition of acetic acid (50 mL). The resultant mixture was then concentrated under reduced pressure, and the residue purified using flash chromatography on silica (60-120), using MDC as eluant.

Intermediate 20

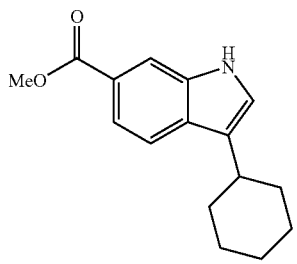

Methyl 3-cyclohexyl-1H-indole-6-carboxylate. Cyclohexanone (42.46 mL, 0.40 mol) was added in a single portion to a stirred solution of methyl indole-6-carboxylate (47.8 g, 0.27 m) in dry dichloromethane (500 mL). The reaction mixture was then cooled to 10° C. and trifluoroacetic acid (63.13 mL, 0.8 m) was added dropwise followed by triethyl silane (174.5 mL, 1.09 m). Upon addition, the temperature was allowed to rise to rt, after which it was stirred for a further 12 h. Dichloromethane (200 mL) was then added and the reaction mixture was washed successively with 10% sodium bicarbonate solution and brine. The organic layer dried over sodium sulfate, filtered and concentrated under vacuum. The resultant residue was purified by flash chromatography on silica (60-120) using hexane-ethyl acetate (9.5:0.5) mixture as eluant. Homogeneous fractions were combined and evaporated to give 60 g of the desired product (85%). Analytical data on this material was consistant with that observed with a sample prepared by the alternative route described above.

Intermediate 21

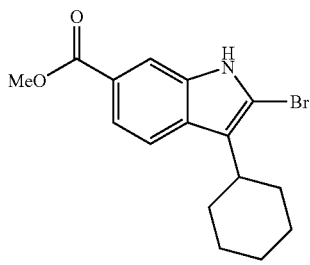

Methyl 2-bromo-3-cyclohexyl-2-1H-indole-6-carboxylate. Dry pyridinium tribromide (12.0 g, 38 mmol) was added in one portion to a stirred and cooled (ice/water bath) solution of methyl 3-cyclohexyl-1H-indole-6-carboxylate (7.71 g, 30 mmol) in a mixture of THF (80 mL) and chloroform (80 mL). The flask was removed from the cooling bath and stirring was continued for 2 hours at room temperature. The mixture was sequentially washed with 1M NaHSO$_3$ (2×50 mL) and 1N HCl (50 mL). It was then dried over anhydrous sodium sulfate, filtered, and concentrated. The concentrate was treated with hexanes and the resulting precipitate was collected by filtration to provide the desired product as an off-white solid (5.8 g, 58%). $^1$H NMR (300 MHz, CDCl$_3$) δ 1.38 (m, 3H), 1.85 (m, 7H), 2.81 (m, 1H), 7.71 (m, 2H), 8.03 (s, 1H), 8.47 (s, 1H).

The hexane mother liquor was concentrated and the residue was dissolved in hexane/ethyl acetate (5:1). The solution was passed through a pad of silica gel with the same solvents. Concentration of the eluate followed by the addition of hexane (10 mL) resulted in the precipitation of additional product which was collected by filtration to provide 2.8 g (28%) of the desired product.

Intermediate 22

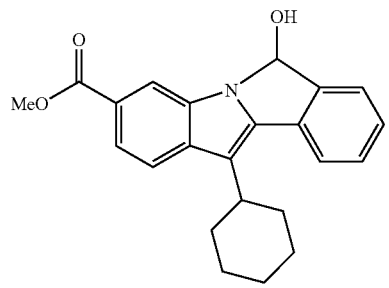

Methyl 11-cyclohexyl-6-hydroxy-6H-isoindolo[2,1-a]indole-3-carboxylate. A stirred mixture of methyl 2-bromo-3-cyclohexyl-1H-indole-6-carboxylate (10.1 g, 30 mmol), 2-formylphenylboronic acid (5.4 g, 36 mmol), LiCl (3.8 g (90 mmol) and Pd (PPh$_3$)$_4$ (1.6 g, 1.38 mmol) in 1M Na$_2$CO$_3$ (40 mL) and 1:1 EtOH-toluene (180 mL) was heated under nitrogen at 85° C. for 3 hours. The reaction mixture was then cooled to RT, and extracted with EtOAc (2×100 mL). The extracts were washed sequentially with water and brine, then dried (MgSO$_4$), filtered and conventrated in-vacuo to afforded 13.3 g of crude product. This material was triturated with DCM and hexanes to provide pure desired product (7.52 g, 70%). LC-MS: m/e 360 (M−H); 344 (M−17) $^+$. $^1$H NMR (400 MHz, CHLOROFORM-D) δ ppm 1.33-1.60 (m, 4H) 1.77-2.01 (m, 6H) 2.80 (d, J=11.83 Hz, 1H) 3.02-3.18 (m, 1H) 3.89 (s, 3H) 6.49 (d, J=11.33 Hz, 1H) 7.34 (t, J=7.55 Hz, 1H) 7.46 (t, J=7.55 Hz, 1H) 7.62 (d, J=7.30 Hz, 1H) 7.66-7.74 (m, 2H) 7.77 (d, J=7.81 Hz, 1H) 8.21 (s, 1H).

Intermediate 23

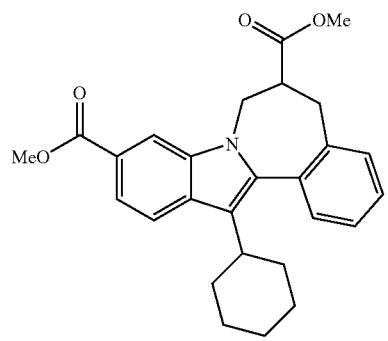

Methyl 13-cyclohexyl-6-(methoxycarbonyl)-7H-indolo[2,1-a][2]benzazepine-10-carboxylate. A stirred suspension of methyl 11-cyclohexyl-6-hydroxy-6H-isoindolo[2,1-a]indole-3-carboxylate (3.61 g, 10 mmol), Cs$_2$CO$_3$ (3.91 g, 12 mmol) and trimethyl 2-phosphonoacetate (2.86 g, 14 mmol) in an. DMF (40 mL) was heated at 60° C. under nitrogen for 3 h. The resultant yellow suspension was cooled to rt and water was added with vigorous stirring. A yellow precipitate formed which was collected by filtration. The solid was washed with water, and then air dried overnight to afford the title compound as a yellow powder (4.124 g, 96%). LC/MS: m/e 430 (MH+); 1H NMR (400 MHz, CHLOROFORM-D) δ ppm 1.30-1.46 (m, J=14.86 Hz, 2H) 1.55 (s, 2H) 1.77 (s, 2H) 1.85-2.18 (m, 4H) 2.76-2.89 (m, 1 H) 3.84 (s, 3H) 3.95 (s, 3H) 4.19 (s, 1H) 5.68 (s, 1H) 7.38-7.63 (m, 4H) 7.74 (dd, J=8.44, 1.39 Hz, 1H) 7.81-7.98 (m, 2H) 8.29 (d, J=11.1 Hz, 1H).

Intermediate 24

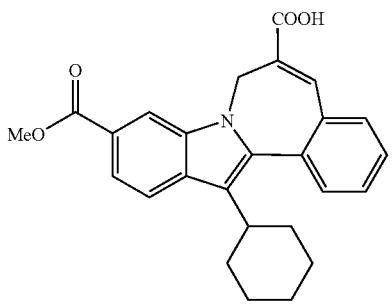

Methyl 13-cyclohexyl-6-(carboxy)-5H-indolo[2,1-a][2]benzazepine-10-carboxylate. Methyl 13-cyclohexyl-6-(methoxycarbonyl)-7H-indolo[2,1-a][2]benzazepine-10-carboxylate (308 mg, 0.72 mmol) was dissolved in N,N-dimethylformamide (5 mL) and treated with LiOH (173 mg, 7.2 mmol). The mixture was heated at 50° C. for 4 hr, after which the solvent was removed in vacuo. The residue was dissolved in H$_2$O (5 mL) and the resultant mixture was acidified by the addition of a 10% aqueous HCL solution. A precipitate formed which was collected by filtration and air dried to afford the title compound as a bright yellow solid (290 mg, 97%). ESI-MS m/z [M+1]=415.

The general methods below were used with the following experimental procedures until indicated otherwise: LCMS data: Stop time: Gradient time+1 minute; Starting conc: 0% B unless otherwise noted; Eluent A: 5% CH$_3$CN/95% H$_2$O with 10 mM NH$_4$OAc (for columns A and D); 10% MeOH/90% H$_2$O with 0.1% TFA (for columns B and C); Eluent B: 95% CH$_3$CN/5% H$_2$O with 10 mM NH$_4$OAc (for columns A and D); 90% MeOH/10% H$_2$O with 0.1% TFA (for columns B and C); Column A: Phenomenex 10 4.6×50 mm C18; Column B: Phenomenex C18 10 3.0×50 mm; Column C: Phenomenex 4.6×50 mm C18 10μ; Column D: Phenomenex Lina C18 5μ 3.0×50 mm; Column E: Phenomenex 5μ 4.6×5.0 mm C18. To a slurried solution of methyl 2-bromo-3-cyclohexyl-1H-indole-6-carboxylate (4.3 g, 13 mmol), 4-methoxy-2-formylphenylboronic acid (3.0 g, 17 mmol) and LiCl (2.2 g, 51 mmol) in EtOH/toluene (1:1, 100 mL) was added Pd(PPh$_3$)$_4$ (1.4 g, 1.3 mmol) and then 1M Na$_2$CO$_3$ (aq.) (32 mL, 32 mmol). The reaction solution was flushed with nitrogen and heated at 100° C. for 3 h and cooled to rt. The reaction was concentrated to remove EtOH, diluted with H$_2$O (200 mL) and extracted with EtOAc (2×150 mL). The combined organics were washed with brine (100 mL), dried (MgSO$_4$), filtered and concentrated to dryness. The residue was triturated with CH$_2$Cl$_2$ and the solids were collected by filtrated and washed with Et$_2$O and CH$_2$Cl$_2$ to yield methyl 11-cyclohexyl-6-hydroxy-8-methoxy-6H-isoindolo[2,1-a]indole-3-carboxylate (3.0 g, 8.0 mmol, 63%) as a yellow solid which was used without further purification. LCMS: m/e 374 (M+H)+, ret time 3.09 min, column B, 3 minute gradient.

Intermediate 25

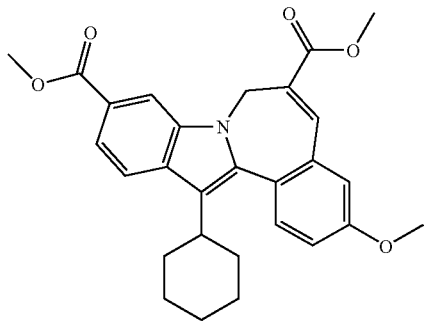

A solution of methyl 11-cyclohexyl-6-hydroxy-8-methoxy-6H-isoindolo[2,1-a]indole-3-carboxylate (2.9 g, 7.4 mmol), methyl 2-(dimethoxyphosphoryl)acrylate (2.6 g, 11 mmol), cesium carbonate (3.6 g, 11 mmol) in DMF (20 mL) was heated at 60° C. for 2 h and cooled to rt. The stirring reaction mixture was diluted with H$_2$O (50 mL) and the precipitates were collected by filtration to yield dimethyl 13-cyclohexyl-3-methoxy-7H-indolo[2,1-a][2]benzazepine-6,10-dicarboxylate (3.3 g, 7.1 mmol, 97%) as a yellow solid which was used without further purification. LCMS: m/e 460 (M+H)+, ret time 3.35 min, column B, 3 minute gradient.

Intermediate 26

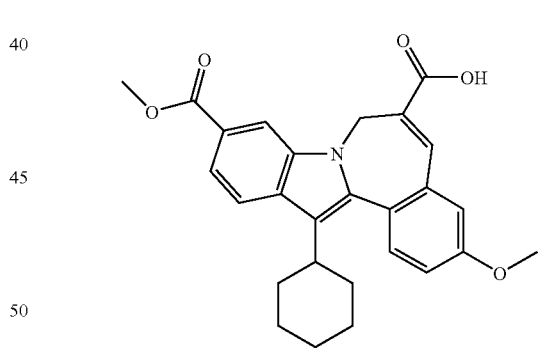

A solution of tetrabutylammonium hydroxide (1M in MeOH, 2.2 mL, 2.2 mmol) was added to a stirring solution of dimethyl 13-cyclohexyl-3-methoxy-7H-indolo[2,1-a][2]benzazepine-6,10-dicarboxylate (1.0 g, 2.2 mmol) in THF (75 mL) and stirred at rt overnight. The reaction mixture was concentrated to ~30 mL, diluted with EtOAc (120 mL), washed with 0.5 M HCl (aq.) (2×50 mL) and brine (40 mL), dried (MgSO$_4$), filtered and concentrated to dryness to yield methyl 7H-indolo[2,1-a][2]benzazepine-10-carboxylate, 13-cyclohexyl, 3-methoxy, 6-carboxylic acid (1.0 g, 2.2 mmol, quant.) as a yellow solid which was used without further purification. LCMS: m/e 446 (M+H)+, ret time 1.54 min, column A, 2 minute gradient.

Intermediate 27

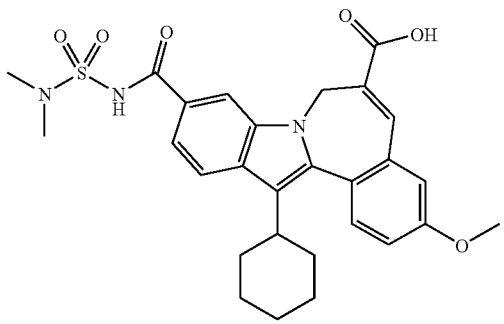

Added 1M NaOH (aq.) (5 mL, 5 mmol) to a solution of methyl 13-cyclohexyl-N-[(dimethylamino)sulfonyl]-3-methoxy-7H-indolo[2,1-a][2]benzazepine-6-carboxylate-10-carboxamide (900 mg, 1.6 mmol) in THF/MeOH (1:1, 14 mL) and heated the reaction mixture in a sealed tube with microwave irradiation at 85° C. for 30 min. The reaction was cooled, neutralized with 1M HCl (aq.) (5 mL, 5.0 mmol) and concentrated to remove organic solvents. The residue was slurried with $H_2O$ and the solids were collected by filtration, flushed with $H_2O$ and dried to yield 13-cyclohexyl-N-[(dimethylamino)sulfonyl]-3-methoxy-7H-indolo[2,1-a][2]benzazepine-10-carboxamide-6-carboxylic acid (807 mg, 1.5 mmol, 92%) as a yellow solid. LCMS: m/e 536 (M–H)⁻, ret time 2.18 min, column A, 4 minute gradient.

The general methods described below pertain to the experimental data for the compounds in the Table 3. LCMS data: Gradient time: 2 min; Flow rate: 4 mL/min;

Stop time Gradient time+2 minute; Starting conc: 0% B; Eluent A: 10% MeOH/90% $H_2O$ with 0.1% TFA; Eluent B: 90% MeOH/10% $H_2O$ with 0.1% TFA; Column 1: Phenomenex 10μ C18 4.6×50 mm.

TABLE 3

| Compound | Analytical Data |
|---|---|
|  | LCMS: m/z 460 (MH⁺), ret time 3.05 min |
|  | LCMS: m/z 446 (MH⁺), ret time 2.89 min |
|  | LCMS: m/z 508 (MH⁺), ret time 2.08 min |

TABLE 3-continued

| Compound | Analytical Data |
|---|---|
| [structure] | LCMS: m/z 429 (MH+), ret time 2.34 min |
| [structure] | LCMS: m/z 522 (MH+), ret time 2.49 min |
| [structure] | LCMS: m/z 538 (MH+), ret time 2.13 min |
| [structure] | LCMS: m/z 540 (MH+), ret time 2.12 min |

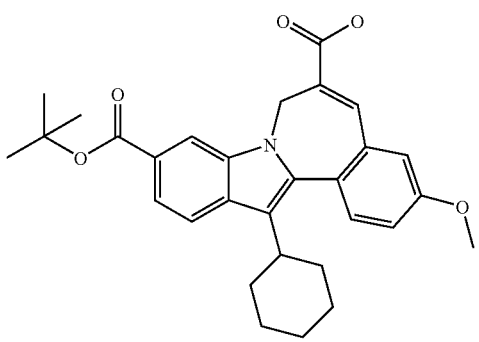

10-(tert-Butoxycarbonyl)-13-cyclohexyl-3-methoxy-7H-indolo[2,1-a][2]benzazepine-6-carboxylic acid. Tetrabutylammonium hydroxide (40% in water, 14.4 mL, 22 mmol) was added to a slurry of 10-tert-butyl 6-methyl 13-cyclohexyl-3-methoxy-7H-indolo[2,1-a][2]benzazepine-6,10-dicarboxylate (5.0 g, 10 mmol) in MeOH (40 mL) and THF (40 mL) and the reaction was stirred at rt ON (complete by LCMS). The reaction mixture was neutralized with 1N HCl (aq) (24 mL) and concentrated to remove the organic solvents. The sludge was diluted with water, stirred and the solids were collected by filtration. The wet solids were dissolved into EtOAc (~250 mL), washed with brine (100 mL), dried ($MgSO_4$), filtered and concentrated to yield 10-(tert-butoxycarbonyl)-13-cyclohexyl-3-methoxy-7H-indolo[2,1-a][2]benzazepine-6-carboxylic acid (5.73 g, 11.8 mmol, 118% yield) as a bright yellow solid. The product appears to be mixed with a tetrabutylammonium by-product. The material was used without further purification. $^1$HNMR (300 MHz, $CDCl_3$) δ ppm 1.14-2.13 (m, 10H), 1.60 (s, 9H), 2.73-2.86 (m, 1H), 3.89 (s, 3H), 4.03-4.26 (m, 1H), 5.49-5.80 (m, 1H), 6.98 (d, J=2.6 Hz, 1H), 7.07 (dd, J=8.4, 2.6 Hz, 1H), 7.56 (d, J=8.4 Hz, 1H), 7.64 (dd, J=8.4, 1.1 Hz, 1H), 7.79 (d, J=8.4 Hz, 1H), 7.89 (br s, 1H), 8.19 (s, 1H. LC-MS retention time: 4.32 min; 488 m/z (MH +). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 mL/min, a gradient of 100% solvent A/0% solvent B to 0% solvent A/100% solvent B, a gradient time of 4 min, a hold time of 1 min, and an analysis time of 5 min where solvent A was 10% MeOH/90% $H_2O$/0.1% trifluoroacetic acid and solvent B was 10% $H_2O$/90% MeOH/0.1% trifluoroacetic acid. MS data was determined using a Micromass Platform for LC in electrospray mode.

EXAMPLE 1

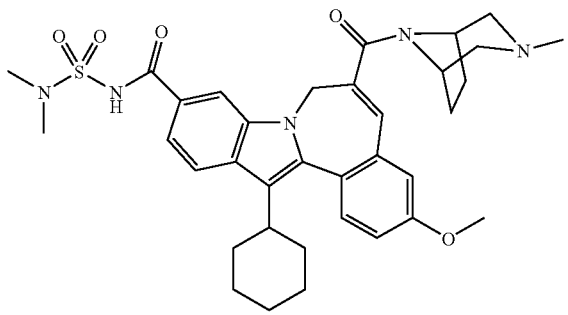

7H-Indolo[2,1-a][2]benzazepine-10-carboxamide, 13-cyclohexyl-N-[(dimethylamino)sulfonyl]-3-methoxy-6-[(3-methyl-3,8-diazabicyclo[3.2.1]oct-8-yl)carbonyl]-. To a stirred solution of 13-cyclohexyl-N-[(dimethylamino)sulfonyl]-3-methoxy-7H-indolo[2,1-a][2]benzazepine-10-carboxamide-6-carboxylic acid (51 mg, 0.095 mmol), 3-methyl-3,8-diazabicyclo[3.2.1]octane dihydrochloride (34 mg, 0.17 mmol) and triethylamine (0.06 mL) in DMF (1.0 mL) was added HATU (50 mg, 0.13 mmol). The reaction mixture was stirred at rt for 2 h, diluted with MeOH (~1 mL) and purified by preparative HPLC ($CH_3CN/H_2O$ with 10 mM $NH_4OAc$) to yield 7H-indolo[2,1-a][2]benzazepine-10-carboxamide, 13-cyclohexyl-N-[(dimethylamino)sulfonyl]-3-methoxy-6-[(3-methyl-3,8-diazabicyclo[3.2.1]oct-8-yl)carbonyl]-(52 mg, 0.08 mmol, 85%) as a yellow solid. $^1$HNMR (300 MHz, $CDCl_3$) δ 8.31 (s, 1H), 7.83 (d, J=8.4 Hz, 1H), 7.59 (br d, J=8.4 Hz, 1H), 7.45 (d, J=8.8 Hz, 1H), 7.02 (dd, J=2.6, 8.8 Hz, 1H), 6.91-6.86 (m, 2H), 5.35-5.16 (m, 1H), 4.34-4.16 (m, 1H), 3.87 (s, 3H), 3.01 (s, 6H), 2.85-1.03 (m, 24H). LCMS: m/e 644 (M–H)$^-$, ret time 2.89 min, column A, 4 minute gradient.

EXAMPLE 2

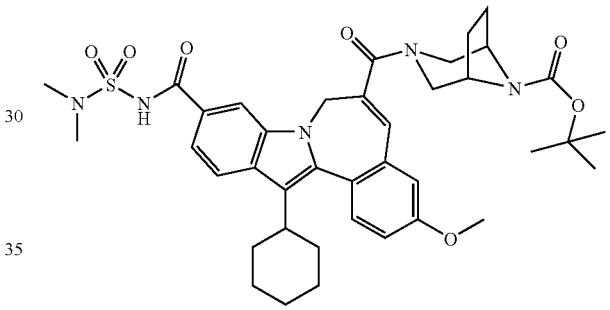

3,8-Diazabicyclo[3.2.1]octane-8-carboxylic acid, 3-[[13-cyclohexyl-10-[[[(dimethylamino)sulfonyl]amino]carbonyl]-3-methoxy-7H-indolo[2,1-a][2]benzazepin-6-yl]carbonyl]-, 1,1-dimethylethyl ester. To a stirred solution of 13-cyclohexyl-N-[(dimethylamino)sulfonyl]-3-methoxy-7H-indolo[2,1-a][2]benzazepine-10-carboxamide-6-carboxylic acid (300 mg, 0.56 mmol), tert-butyl 3,8-diazabicyclo[3.2.1]octane-8-carboxylate (150 mg, 0.71 mmol) and triethylamine (0.25 mL) in DMF (2.5 mL) was added HATU (250 mg, 0.66 mmol). The reaction mixture was stirred at rt for 1 h, diluted with $H_2O$ (~10 mL), acidified with 1M HCl (aq.). (~0.5 mL) and the precipitate was collected by filtration and flushed with $H_2O$. The solids were dissolved into MeOH/DMF (1:1) and purified by preparative HPLC ($CH_3CN/H_2O$ with 10 mM $NH_4OAc$) to yield 3,8-diazabicyclo[3.2.1]octane-8-carboxylic acid, 3-[[13-cyclohexyl-10-[[[(dimethylamino)sulfonyl]amino]carbonyl]-3-methoxy-7H-indolo[2,1-a][2]benzazepin-6-yl]carbonyl]-, 1,1-dimethylethyl ester (130 mg, 0.18 mmol, 32%) as a yellow solid. $^1$HNMR (300 MHz, $CDCl_3$) δ 8.85 (br s, 1H), 8.08 (s, 1H), 7.85 (d, J=8.4 Hz, 1H), 7.47 (d, J=8.4 Hz, 1H), 7.44 (d, J=8.8 Hz, 1H), 7.03 (dd, J=2.6, 8.8 Hz, 1H), 6.86 (d, J=2.6 Hz, 1H), 6.75 (s, 1H), 5.25-5.00 (m, 1H), 4.49-4.01 (m, 3H), 3.88 (s, 3H), 3.35-2.90 (m, 2H), 3.03 (s, 6H), 2.86-2.72 (m, 1H), 2.12-1.12 (m, 16H), 1.41 (s, 9H). LCMS: m/e 730 (M–H)$^-$, ret time 3.41 min, column A, 4 minute gradient.

EXAMPLE 3

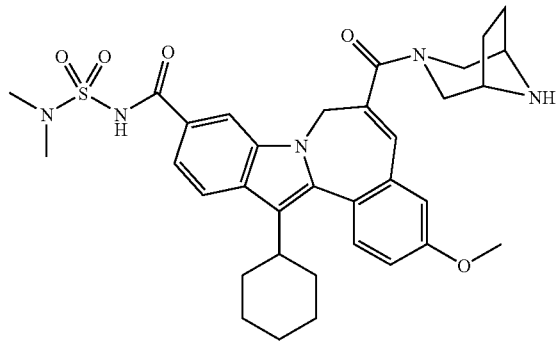

7H-Indolo[2,1-a][2]benzazepine-10-carboxamide, 13-cyclohexyl-6-(3,8-diazabicyclo[3.2.1]oct-3-ylcarbonyl)-N-[(dimethylamino)sulfonyl]-3-methoxy-.

To a solution of 3,8-diazabicyclo[3.2.1]octane-8-carboxylic acid, 3-[[13-cyclohexyl-10-[[[(dimethylamino)sulfonyl]amino]carbonyl]-3-methoxy-7H-indolo[2,1-a][2]benzazepin-6-yl]carbonyl]-, 1,1-dimethylethyl ester (103 mg, 0.14 mmol) in $CH_2Cl_2$ (2 mL) was added trifluoroacetic acid (2 mL). The reaction mixture was stirred at rt for 2 h, concentrated, dissolved into MeOH (2 mL) and purified by preparative HPLC ($CH_3CN/H_2O$ with 10 mM $NH_4OAc$) to yield 7H-indolo[2,1-a][2]benzazepine-10-carboxamide, 13-cyclohexyl-6-(3,8-diazabicyclo[3.2.1]oct-3-ylcarbonyl)-N-[(dimethylamino)sulfonyl]-3-methoxy- (77 mg, 0.12 mmol, 87%) as a light yellow solid. $^1$HNMR (300 MHz, $d_6$-DMSO) δ 8.24 (s, 1H), 7.78 (d, J=8.4 Hz, 1H), 7.67 (d, J=8.4 Hz, 1H), 7.50 (d, J=8.4 Hz, 1H), 7.22-7.14 (m, 2H), 6.95 (s, 1H), 5.19-4.95 (m, 1H), 4.42-4.20 (m, 1H), 3.87 (s, 3H), 3.82-2.98 (m, 7H), 2.82-2.68 (m, 1H), 2.75 (s, 6H), 2.14-0.93 (m, 14H), 1.41 (s, 9H). LCMS: m/e 630 (M−H)$^-$, ret time 2.54 min, column A, 4 minute gradient.

EXAMPLE 4

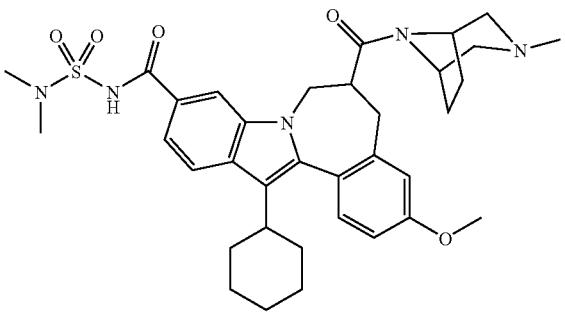

5H-Indolo[2,1-a][2]benzazepine-10-carboxamide, 13-cyclohexyl-N-[(dimethylamino)sulfonyl]-6,7-dihydro-3-methoxy-6-[(3-methyl-3,8-diazabicyclo[3.2.1]oct-8-yl)carbonyl]-. 10% Palladium on carbon (47 mg, 0.05 mmol) was added to a solution of 7H-indolo[2,1-a][2]benzazepine-10-carboxamide, 13-cyclohexyl-N-[(dimethylamino)sulfonyl]-3-methoxy-6-[(3-methyl-3,8-diazabicyclo[3.2.1]oct-8-yl)carbonyl]-(52 mg, 0.086 mmol) in MeOH (3 mL) and the reaction mixture was vacuum flushed with nitrogen (3x) and then with hydrogen (4x). The reaction was stirred under a balloon of hydrogen overnight. The reaction was diluted with $CH_2Cl_2$ (1 mL), additional 10% palladium on carbon (30 mg, 0.03 mmol) was added and the reaction mixture was vacuum flushed with nitrogen (3x) and then with hydrogen (4x). The reaction was stirred under a balloon of hydrogen for 2d, filtered through a pad of celite and concentrated. The residue was dissolved into MeOH and purified by preparative HPLC ($CH_3CN/H_2O$ with 10 mM $NH_4OAc$) to yield 5H-indolo[2,1-a][2]benzazepine-10-carboxamide, 13-cyclohexyl-N-[(dimethylamino)sulfonyl]-6,7-dihydro-3-methoxy-6-[(3-methyl-3,8-diazabicyclo[3.2.1]oct-8-yl)carbonyl]-(17 mg, 0.026 mmol, 40%) as a yellow solid. Mixture of atrope diastereomers. $^1$HNMR (300 MHz, CDCl$_3$) δ 8.16-7.77 (m, 2H), 7.51-7.41 (m, 1H), 7.37-7.27 (m, 1H), 7.07-6.74 (m, 2H), 4.77-4.05 (m, 3H), 3.91-3.81 (m, 3H), 3.77-3.17 (m, 1H), 3.07-2.99 (m, 6H), 2.95-1.09 (m, 25H). LCMS: m/e 648 (M−H)$^-$, ret time 2.93 min, column A, 4 minute gradient.

EXAMPLE 5

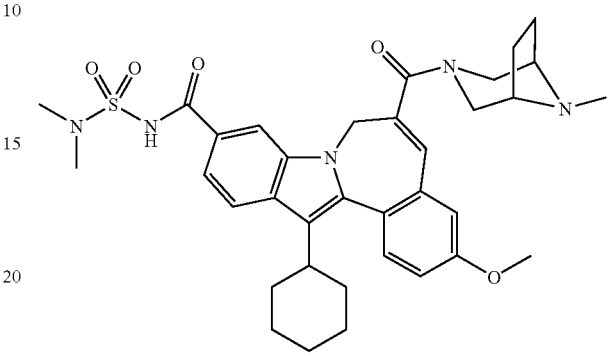

7H-Indolo[2,1-a][2]benzazepine-10-carboxamide, 13-cyclohexyl-N-[(dimethylamino)sulfonyl]-3-methoxy-6-[(8-methyl-3,8-diazabicyclo[3.2.1]oct-3-yl)carbonyl]-. To a stirring solution of 7H-indolo[2,1-a][2]benzazepine-10-carboxamide, 13-cyclohexyl-6-(3,8-diazabicyclo[3.2.1]oct-3-ylcarbonyl)-N-[(dimethylamino)sulfonyl]-3-methoxy- (44 mg, 0.070 mmol) in MeOH/$CH_2Cl_2$ (1:1, 4 mL) at rt was added NaCNBH$_3$ (30 mg 0.48 mmol) and then formaldehyde (37 wt % in H$_2$O, 0.10 mL, 3.6 mmol). The reaction mixture was stirred for 30 min and concentrated to dryness. The residue was dissolved into MeOH and purified by preparative HPLC ($CH_3CN/H_2O$ with 10 mM $NH_4OAc$) to yield 7H-indolo[2,1-a][2]benzazepine-10-carboxamide, 13-cyclohexyl-N-[(dimethylamino)sulfonyl]-3-methoxy-6-[(8-methyl-3,8-diazabicyclo[3.2.1]oct-3-yl)carbonyl]-(31 mg, 0.047 mmol, 68%) as a yellow solid. $^1$HNMR (300 MHz, CDCl$_3$) δ 8.11 (s, 1H), 7.79 (d, J=8.4 Hz, 1H), 7.66-7.60 (m, 2H), 7.52 (d, J=8.8 Hz, 1H), 7.11 (dd, J=2.6, 8.8 Hz, 1H), 7.00 (dd, J=2.6 Hz, 1H), 6.87 (s, 1H), 5.23-5.04 (m, 1H), 4.48-4.26 (m, 1H), 3.92 (s, 3H), 3.38-2.77 (m, 7H), 3.03 (s, 6H), 2.25 (br s, 3H), 2.16-1.15 (m, 14H). LCMS: m/e 644 (M−H)$^-$, ret time 2.69 min, column A, 4 minute gradient.

EXAMPLE 6

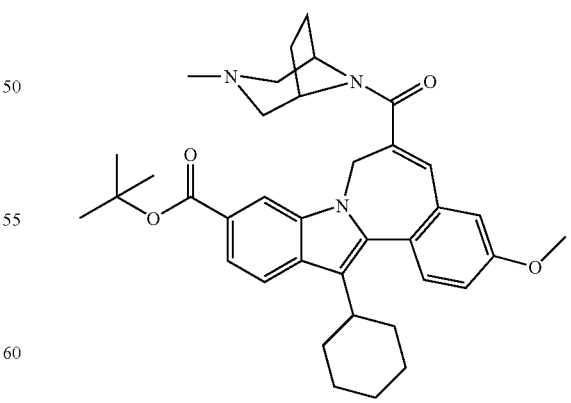

tert-Butyl 13-cyclohexyl-3-methoxy-6-((3-methyl-3,8-diazabicyclo[3.2.1]oct-8-yl)carbonyl)-7H-indolo[2,1-a][2]benzazepine-10-carboxylate. HATU (680 mg, 1.8 mmol) was added to a stirring solution of 10-(tert-butoxycarbonyl)-13-cyclohexyl-3-methoxy-7H-indolo[2,1-a][2]benzazepine-6- carboxylic acid (670 mg, 1.37 mmol) and 3-methyl-3,8-diazabicyclo[3.2.1]octane di HCl salt (560 mg, 2.81 mmol) in DMF (6 mL) and TEA (1.2 mL, 8.2 mmol) and the reaction was stirred for 30 min (complete by LCMS). The reaction mixture was diluted with water (~35 mL) (precipitate formed) and stirred ON. The precipitate was collected by filtration, flushed with water and dried under high vacuum at 55° C. to yield tert-butyl 13-cyclohexyl-3-methoxy-6-((3-methyl-3,8-diazabicyclo[3.2.1]oct-8-yl)carbonyl)-7H-indolo[2,1-a][2]benzazepine-10-carboxylate (775 mg, 1.30 mmol, 95% yield) as a light yellow solid. The material was used without further purification. $^1$HNMR (300 MHz, CDCl$_3$) δ ppm 1.14-3.95 (m, 24H), 1.59 (s, 9H), 3.86 (s, 3H), 4.21-5.26 (m, 2H), 6.82 (s, 1H), 6.88 (d, J=2.6 Hz, 1H), 7.01 (dd, J=8.8, 2.6 Hz, 1H), 7.47 (d, J=8.8 Hz, 1H), 7.66 (dd, J=8.4, 1.1 Hz, 1H), 7.80 (d, J=8.4 Hz, 1H), 8.02 (br s, 1H). LC-MS retention time: 3.72 min; m/z 596 (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 mL/min, a gradient of 100% solvent A/0% solvent B to 0% solvent A/100% solvent B, a gradient time of 4 min, a hold time of 1 min, and an analysis time of 5 min where solvent A was 10% MeOH/90% H$_2$O/0.1% trifluoroacetic acid and solvent B was 10% H$_2$O/90% MeOH/0.1% trifluoroacetic acid. MS data was determined using a Micromass Platform for LC in electrospray mode.

EXAMPLE 7

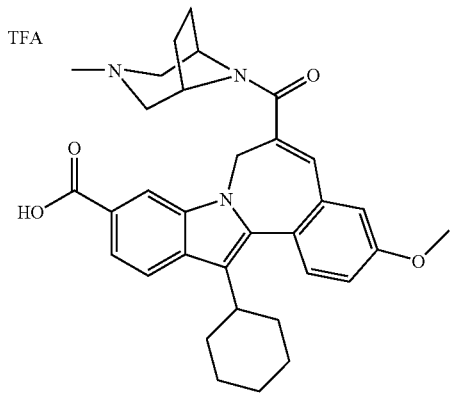

13-Cyclohexyl-3-methoxy-6-((3-methyl-3,8-diazabicyclo[3.2.1]oct-8-yl)carbonyl)-7H-indolo[2,1-a][2]benzazepine-10-carboxylic acid trifluoroacetate. tert-Butyl 13-cyclohexyl-3-methoxy-6-((3-methyl-3,8-diazabicyclo[3.2.1]oct-8-yl)carbonyl)-7H-indolo[2,1-a][2]benzazepine-10-carboxylate (300 mg, 0.504 mmol) was dissolved into DCE (5 mL) and then TFA (700 µl, 9.09 mmol) was added (reaction became green) and the reaction was stirred at rt for 1 h (~70% conversion by LCMS). More TFA (700 µl, 9.09 mmol) was added and the reaction was stirred 1 h (complete by LCMS). The reaction mixture was concentrated on a rotary evaporator, diluted with diethyl ether and reconcentrated twice to yield 13-cyclohexyl-3-methoxy-6-((3-methyl-3,8-diazabicyclo[3.2.1]oct-8-yl)carbonyl)-7H-indolo[2,1-a][2]benzazepine-10-carboxylic acid trifluoroacetate (362 mg, 0.55 mmol, quant.) as a dark yellow solid. Used without further purification. $^1$HNMR (300 MHz, DMSO-d$_6$) δ ppm 1.06-2.13 (m, 21H), 2.68-2.86 (m, 1H), 3.36-3.50 (m, 2H), 3.90 (s, 3H), 4.11-5.35 (m, 2H), 7.14 (s, 1H), 7.18-7.28 (m, 2H), 7.53 (d, J=8.4 Hz, 1H), 7.61 (dd, J=8.4, 1.1 Hz, 1H), 7.87 (d, J=8.4 Hz, 1H), 8.21 (br s, 1H), 9.55 (br s, 1H). LC-MS retention time: 3.72 min; m/z 596 (MH+). LC-MS retention time: 2.50 min; 538 m/z (MH-). LC data was recorded on a Shimadzu LC-10AS liquid chromatograph equipped with a Phenomenex-Luna 10u C18 4.6×50 mm column using a SPD-10AV UV-Vis detector at a detector wave length of 220 nM. The elution conditions employed a flow rate of 5 mL/min, a gradient of 100% solvent A/0% solvent B to 0% solvent A/100% solvent B, a gradient time of 4 min, a hold time of 1 min, and an analysis time of 5 min where solvent A was 5% acetonitrile/95% H$_2$O/10 mM ammonium acetate and solvent B was 5% H$_2$O/95% acetonitrile/10 mM ammonium acetate. MS data was determined using a Micromass Platform for LC in electrospray mode.

EXAMPLE 8

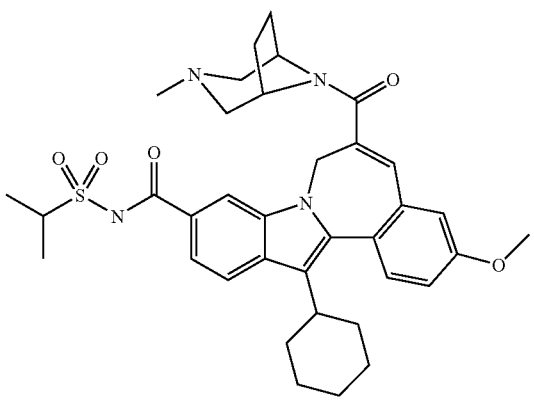

13-Cyclohexyl-N-(isopropylsulfonyl)-3-methoxy-6-((3-methyl-3,8-diazabicyclo[3.2.1]oct-8-yl)carbonyl)-7H-indolo[2,1-a][2]benzazepine-10-carboxamide. CDI (80 mg, 0.49 mmol) was added to a solution of tert-butyl 13-cyclohexyl-3-methoxy-6-((3-methyl-3,8-diazabicyclo[3.2.1]oct-8-yl)carbonyl)-7H-indolo[2,1-a][2]benzazepine-10-carboxylate TFA (200 mg, 0.30 mmol) in THF (1.5 mL) and the reaction mixture was heated at 60° C. for 2 h. The reaction was cooled to rt and then ⅓ (~0.55 mL) of the reaction solution was added to a stirring solution of propane-2-sulfonamide (40 mg, 0.33 mmol) in DBU (0.20 mL, 1.3 mmol) and THF (0.20 mL). The reaction was stirred at rt ON (complete by LCMS), concentrated to an oil, quenched with 1N HCl (~1 mL) (prec. formed) and extracted with EtOAc (2×1 mL). The combined organics wee concentrated to dryness, dissolved into MeOH (1.5 mL) and purified by preparative HPLC (CH$_3$CN/H$_2$O with 10 mM NH$_4$OAc) to yield 13-cyclohexyl-N-(isopropylsulfonyl)-3-methoxy-6-((3-methyl-3,8-diazabicyclo[3.2.1]oct-8-yl)carbonyl)-7H-indolo[2,1-a][2]benzazepine-10-carboxamide (28.5 mg, 0.044 mmol, 43% yield) as a yellow solid. $^1$HNMR (300 MHz, CD$_3$OD) δ ppm 1.13-2.77 (m, 28H), 2.80-2.93 (m, 1H), 3.93 (s, 3H), 3.90-4.02 (m, 1H), 4.27-4.65 (m, 2H), 5.11-5.31 (m, 1H), 7.04 (s, 1H), 7.11 (d, J=2.6 Hz, 1H), 7.16 (dd, J=8.4, 2.6 Hz, 1H), 7.56 (d, J=8.4 Hz, 1H), 7.67 (dd, J=8.4, 1.5 Hz, 1H), 7.88 (d, J=8.4 Hz, 1H), 8.18 (br s, 1H). LC-MS retention time: 2.55 min; m/z 643 (MH-). LC data was recorded on a Shimadzu LC-10AS liquid chromatograph equipped with a Phenomenex-Luna 10u C18 4.6×50 mm column using a SPD-10AV UV-Vis detector at a detector wave length of 220 nM. The elution conditions employed a flow rate of 5 mL/min, a gradient of 100% solvent A/0% solvent B to 0% solvent A/100% solvent B, a gradient time of 4 min, a hold time of 1 min, and an analysis time of 5 min where solvent A was 5% acetonitrile/95% H$_2$O/10 mM ammonium acetate and solvent B was 5% H$_2$O/95% acetonitrile/10 mM ammonium acetate. MS data was determined using a Micromass Platform for LC in electrospray mode.

We claim:
1. A compound of formula I

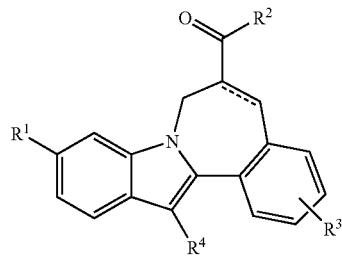

where:
R[1] is $CO_2R^5$ or $CONR^6R^7$;
R[2] is

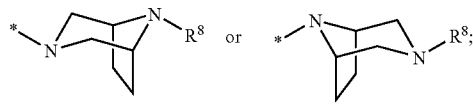

R[3] is hydrogen, halo, alkyl, alkenyl, hydroxy, benzyloxy, alkoxy, or haloalkoxy;
R[4] is cycloalkyl;
R[5] is hydrogen or alkyl;
R[6] is hydrogen, alkyl, alkylSO$_2$, cycloalkylSO$_2$, haloalkylSO$_2$, $(R^9)_2NSO_2$, or $(R^{10})SO_2$;
R[7] is hydrogen or alkyl;
R[8] is hydrogen, alkyl, cycloalkyl, (cycloalkyl)alkyl, alkylcarbonyl, alkoxycarbonyl, benzyl, benzyloxycarbonyl, or pyridinyl;
R[9] is hydrogen or alkyl;
R[10] is azetidinyl, pyrrolidinyl, piperidinyl, N—(R[11])piperazinyl, morpholinyl, thiomorpholinyl, homopiperidinyl, or homomorpholinyl;
R[11] is hydrogen or alkyl; and
the dotted line represents a single bond or a double bond;
or a pharmaceutically acceptable salt thereof.

2. A compound of claim 1 where R[1] is $CONR^6R^7$; R[6] is alkylSO$_2$, cycloalkylSO$_2$, haloalkylSO$_2$, $(R^9)_2NSO_2$, or $(R^{10})SO_2$; and R[7] is hydrogen.

3. A compound of claim 1 where R[3] is hydrogen.

4. A compound of claim 1 where R[3] is methoxy.

5. A compound of claim 1 where R[4] is cyclohexyl.

6. A compound of claim 1 where R[6] is $(R^9)_2NSO_2$ or $(R^{10})SO_2$.

7. A compound of claim 1 where the dotted line represents a single bond.

8. A compound of claim 1 where the dotted line represents a double bond.

9. A compound of claim 1 selected from the group consisting of

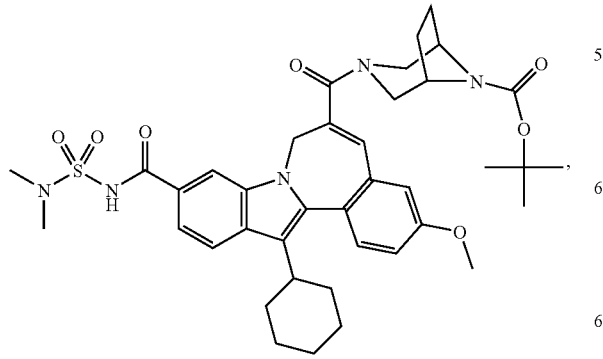

-continued

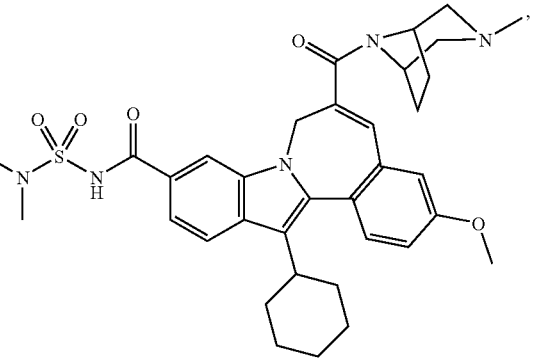

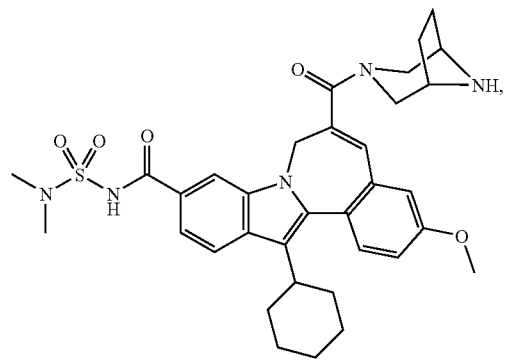

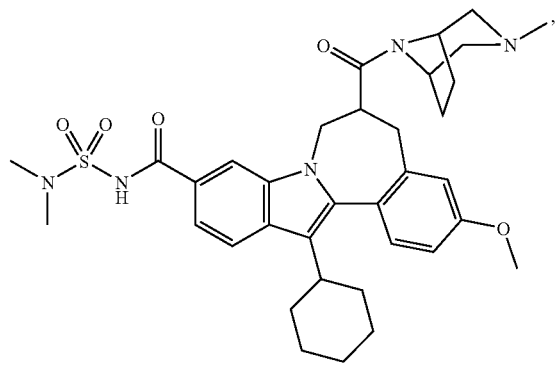

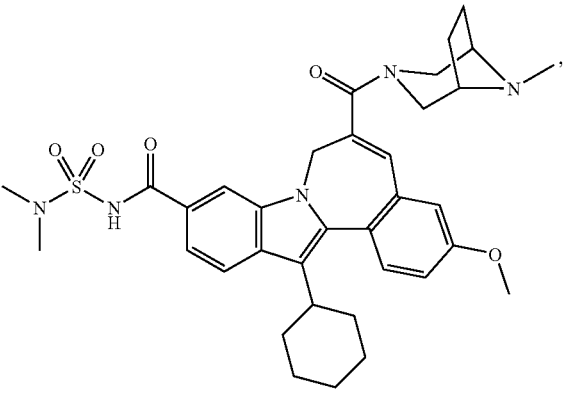

59
-continued
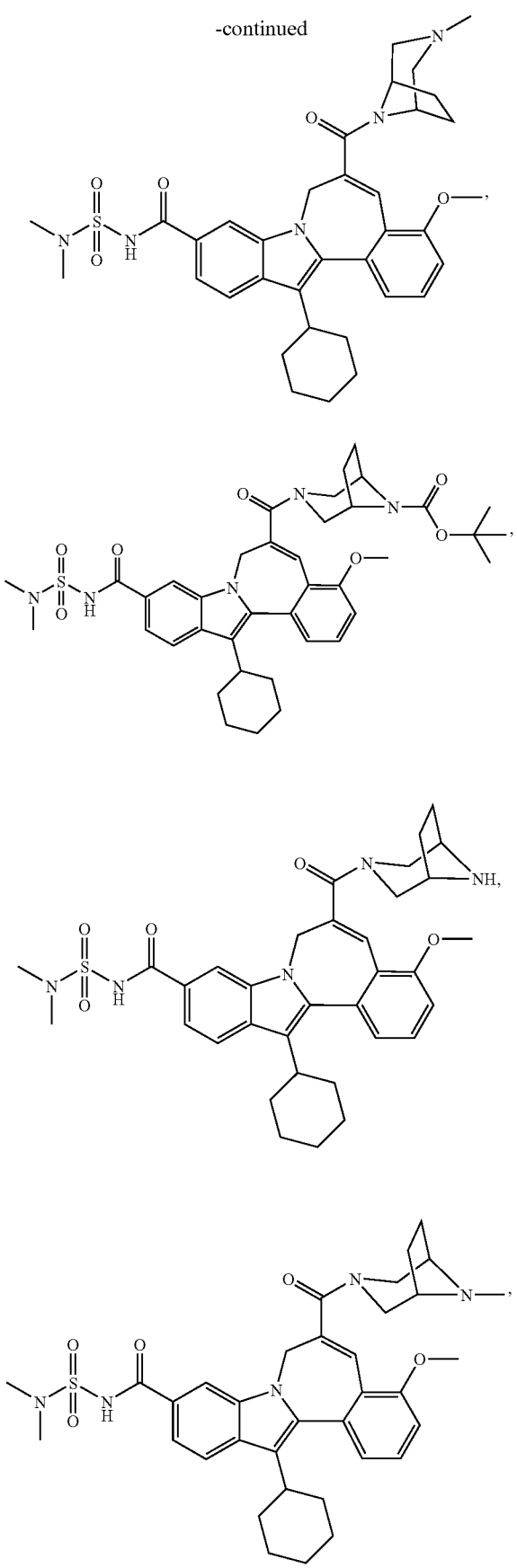
60
-continued
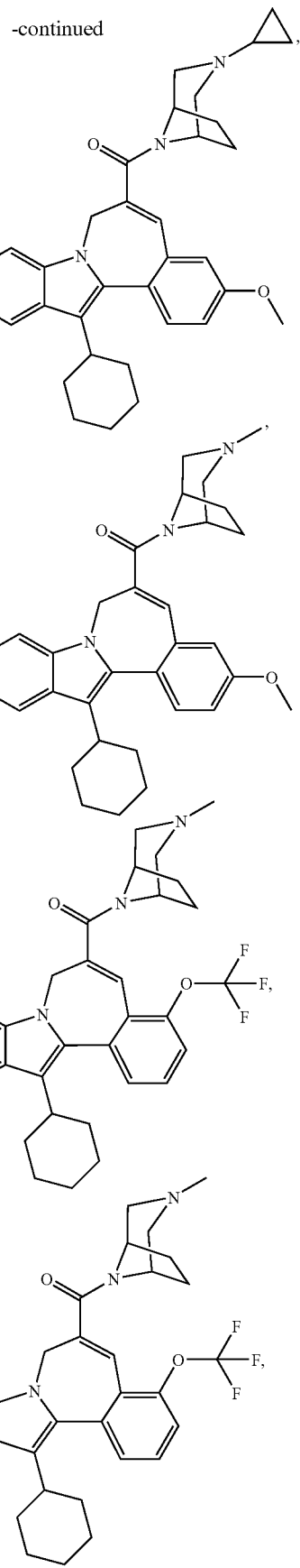

-continued
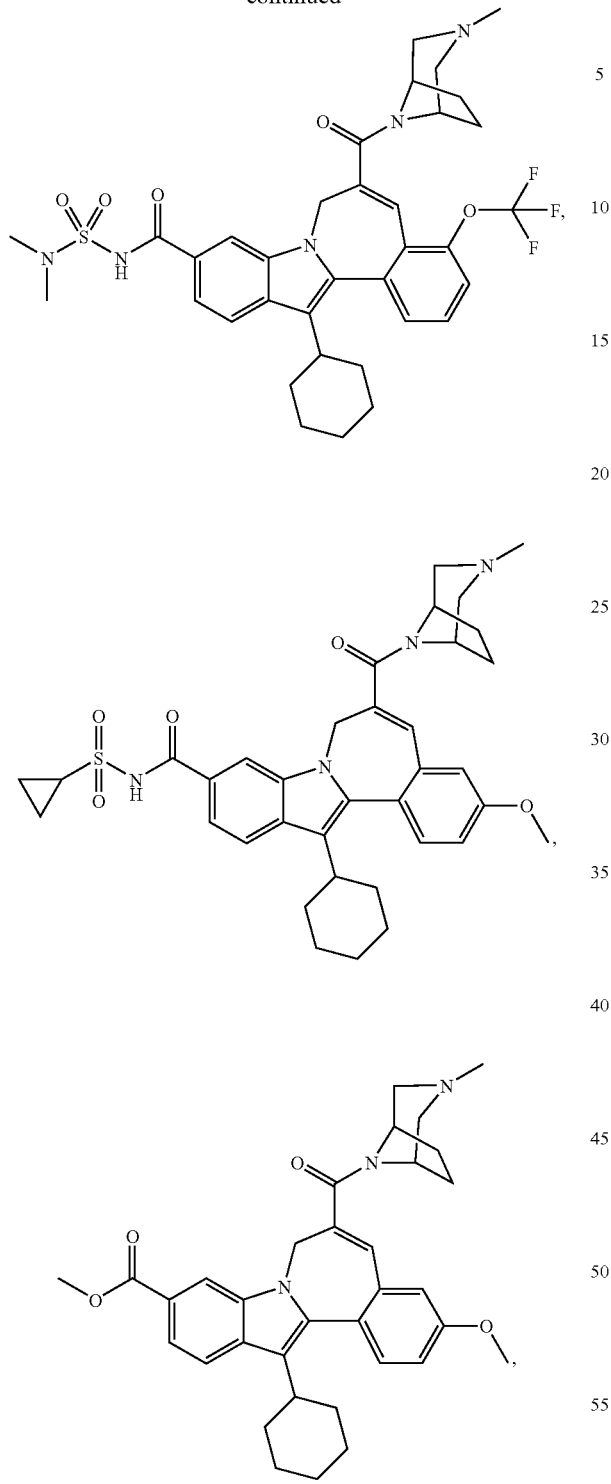
-continued
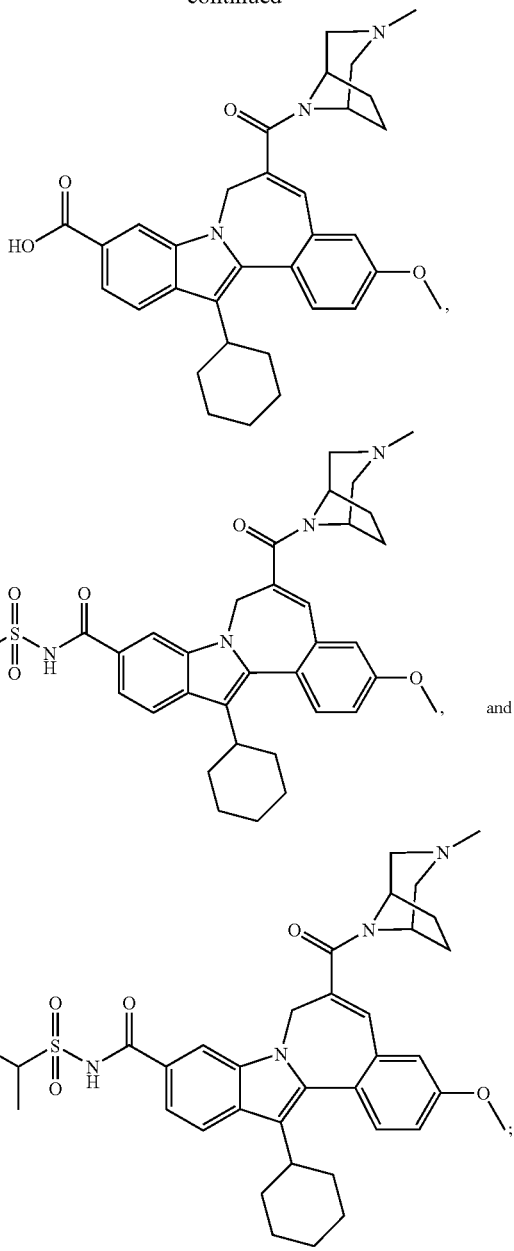
or a pharmaceutically acceptable salt thereof.
10. A composition comprising a compound of claim 1 or a pharmaceutically acceptable salt thereof and a pharmaceutically acceptable carrier.
11. A method of treating hepatitis C infection comprising administering a therapeutically effective amount of a compound of claim 1 to a patient.
* * * * *